(12) United States Patent
Harada et al.

(10) Patent No.: US 11,882,998 B2
(45) Date of Patent: *Jan. 30, 2024

(54) ENDOSCOPE

(71) Applicant: FUJIFILM Corporation, Tokyo (JP)

(72) Inventors: Takashi Harada, Kanagawa (JP); Tomohiro Ohki, Kanagawa (JP); Shozo Iyama, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 544 days.

This patent is subject to a terminal disclaimer.

(21) Appl. No.: 16/744,197

(22) Filed: Jan. 16, 2020

(65) Prior Publication Data
US 2020/0146536 A1    May 14, 2020

Related U.S. Application Data

(63) Continuation of application No. PCT/JP2018/022362, filed on Jun. 12, 2018.

(30) Foreign Application Priority Data

Jul. 18, 2017    (JP) .................................. 2017-139140

(51) Int. Cl.
    *A61B 1/00*    (2006.01)
(52) U.S. Cl.
    CPC ...... *A61B 1/00098* (2013.01); *A61B 1/00133* (2013.01)
(58) Field of Classification Search
    CPC ............ A61B 1/00098; A61B 1/00133; A61B 1/00087; A61B 1/00135; A61B 1/0052;
    (Continued)

(56) References Cited

U.S. PATENT DOCUMENTS 4,198,959 A * 4/1980 Otani ................. A61B 1/00137
                                                        600/153
4,697,576 A    10/1987 Krauter
(Continued)

FOREIGN PATENT DOCUMENTS

CN    102670153    9/2012
CN    105011893    11/2015
(Continued)

OTHER PUBLICATIONS

JPH06319692 English translation (Year: 1994).*
(Continued)

*Primary Examiner* — Michael J Carey
*Assistant Examiner* — Megan Elizabeth Monahan
(74) *Attorney, Agent, or Firm* — JCIPRNET

(57) ABSTRACT

An endoscope is provided in which an attachment/detachment operation of the proximal end of a wire can be easily performed to/from an erecting operation mechanism and the wire can be prevented from meandering in a wire channel. An endoscope has an operation section 22 provided with an erecting operation lever, and a movable member 96 that moves in association with an operation of the erecting operation lever. The movable member 96 is arranged to be exposed to outside of the operation section 22. A wire 60 has a distal end side coupled to an erecting base, and a proximal end side coupled to an attachment member 98 that is attachable to and detachable from the movable member 96 by a one-touch operation. The wire 60 is configured of a wire body 60A and a gap filling member 60B.

17 Claims, 34 Drawing Sheets

(58) Field of Classification Search
CPC .............. A61B 1/0057; A61B 1/00128; A61B 1/00154; A61B 1/01; A61B 2017/0034; A61B 2017/00296
See application file for complete search history.

(56) References Cited

U.S. PATENT DOCUMENTS

| | | | |
|---|---|---|---|
| 5,460,168 | A | 10/1995 | Masubuchi et al. |
| 5,569,157 | A | 10/1996 | Nakazawa et al. |
| 5,609,563 | A | 3/1997 | Suzuki et al. |
| 7,846,090 | B2 | 12/2010 | Pilvisto et al. |
| 8,771,171 | B2 | 7/2014 | Onuki et al. |
| 9,456,736 | B2 | 10/2016 | Onuki et al. |
| 9,974,610 | B2 | 5/2018 | Oguni et al. |
| 10,058,232 | B2* | 8/2018 | Sueyasu ............. A61B 1/00098 |
| 10,165,930 | B2 | 1/2019 | Tanaka et al. |
| 2001/0044570 | A1* | 11/2001 | Ouchi ................. A61B 1/00177 600/107 |
| 2004/0267090 | A1 | 12/2004 | Ueno et al. |
| 2005/0049455 | A1 | 3/2005 | Ootawara et al. |
| 2005/0192475 | A1 | 9/2005 | Okada |
| 2005/0251157 | A1 | 11/2005 | Saadat et al. |
| 2006/0287576 | A1 | 12/2006 | Tsuji et al. |
| 2007/0270638 | A1 | 11/2007 | Kitano et al. |
| 2012/0238815 | A1 | 9/2012 | Komi et al. |
| 2016/0325077 | A1 | 11/2016 | Yamanaka et al. |

FOREIGN PATENT DOCUMENTS

| | | | | |
|---|---|---|---|---|
| CN | 105899116 | | 8/2016 | |
| CN | 105979895 | | 9/2016 | |
| CN | 105982636 | | 10/2016 | |
| EP | 1759626 | | 5/2013 | |
| JP | S48028903 | | 9/1973 | |
| JP | H04108507 | | 4/1992 | |
| JP | H04314439 | | 11/1992 | |
| JP | H06319692 | * | 5/1993 | ............... A61B 1/00 |
| JP | H06254037 | | 9/1994 | |
| JP | H0619692 | * | 11/1994 | |
| JP | H06315456 | | 11/1994 | |
| JP | H06315458 | | 11/1994 | |
| JP | H06315459 | | 11/1994 | |
| JP | H06319692 | * | 11/1994 | |
| JP | H0723900 | | 1/1995 | |
| JP | H0747052 | | 2/1995 | |
| JP | H07111967 | * | 2/1995 | |
| JP | H07111967 | | 5/1995 | |
| JP | H07184830 | | 7/1995 | |
| JP | H07184831 | | 7/1995 | |
| JP | H07184845 | | 7/1995 | |
| JP | H07313446 | | 12/1995 | |
| JP | H0919401 | | 1/1997 | |
| JP | H09329770 | | 12/1997 | |
| JP | H10302435 | | 11/1998 | |
| JP | 2001327464 | | 11/2001 | |
| JP | 2002017663 | | 1/2002 | |
| JP | 2002221671 | | 8/2002 | |
| JP | 2005007148 | | 1/2005 | |
| JP | 2005237659 | | 9/2005 | |
| JP | 2005323662 | | 11/2005 | |
| JP | 2006084374 | | 3/2006 | |
| JP | 2010136737 | * | 12/2008 | ............... A61B 1/00 |
| JP | 2009109779 | | 5/2009 | |
| JP | 2010136737 | * | 6/2010 | |
| WO | 2005082230 | | 9/2005 | |
| WO | 2013099390 | | 7/2013 | |
| WO | WO-2016027574 | A1* | 2/2016 | ......... A61B 1/00098 |
| WO | 2017011535 | | 1/2017 | |
| WO | WO-2017011535 | A1* | 1/2017 | ............... A61B 1/00 |

OTHER PUBLICATIONS

JPH07111967 English translation (Year: 1995).*
WO2016027574 English translation (Year: 2016).*
JP2010136737 English Translation (Year: 2010).*
"Search Report of Europe Counterpart Application", dated Mar. 30, 2021, p. 1-p. 24.
"Office Action of Europe Counterpart Application", dated Mar. 26, 2021, p. 1-p. 6.
Office Action of China Counterpart Application, with English translation thereof, dated Jun. 25, 2021, pp. 1-19.
"Search Report of Europe Counterpart Application", dated Jun. 9, 2020, p. 1-p. 8.
"International Search Report (Form PCT/ISA/210) of PCT/JP2018/022362," dated Jul. 24, 2018, with English translation thereof, pp. 1-5.
"Written Opinion of the International Searching Authority (Form PCT/ISA/237) of PCT/ JP2018/022362," dated Jul. 24, 2018, with English translation thereof, pp. 1-7.
"International Search Report (Form PCT/ISA/210) of PCT/JP2018/022357," dated Aug. 21, 2018, with English translation thereof, pp. 1-6.
"Written Opinion of the International Searching Authority (Form PCT/ISA/237) of PCT/JP2018/022357," dated Aug. 21, 2018, with English translation thereof, pp. 1-12.
"Search Report of Europe Co-Pending Application, U.S. Appl. No. 18/835,377", dated Jun. 9, 2020, pp. 1-7.
"Office Action of China Co-Pending Application, Application No. 201880043059", dated Jun. 25, 2021, with English translation thereof, pp. 1-18.
"Office Action of Japan Co-Pending Application, Application No. 2021019868", with English translation thereof, dated Feb. 1, 2022, pp. 1-8.
"International Search Report (Form PCT/ISA/210) of PCT/JP2018/022358," dated Sep. 4, 2018, with English translation thereof, pp. 1-6.
"Written Opinion of the International Searching Authority (Form PCT/ISA/237) of PCT/JP2018/022358," dated Sep. 4, 2018, with English translation thereof, pp. 1-11.
"Search Report of Europe Co-Pending Application, U.S. Appl. No. 18/835,010", dated Jun. 18, 2020, p. 1-p. 5.
"Office Action of China Co-Pending Application, Application No. 201880043066", dated Jul. 2, 2021, with English translation thereof, pp. 1-16.
"Office Action of Japan Co-Pending Application, Application No. 2020156354", with English translation thereof, dated Aug. 26, 2021, p. 1-p. 7.
"Office Action of China Co-Pending Application, Application No. 201880043177", with English translation thereof, dated Jul. 1, 2021, pp. 1-20.
"International Search Report (Form PCT/ISA/210) of PCT/JP2018/022361," dated Jul. 24, 2018, with English translation thereof, pp. 1-5.
"Written Opinion of the International Searching Authority (Form PCT/ISA/237) of PCT/JP2018/022361," dated Jul. 24, 2018, with English translation thereof, pp. 1-7.
"Search Report of Europe Co-Pending Application, U.S. Appl. No. 18/835,495", dated Jun. 9, 2020, pp. 1-8.
"Office Action of China Co-Pending Application, Application No. 201880043177", with English translation thereof, dated Dec. 28, 2021, pp. 1-20.
"Office Action of Japan Co-Pending Application, Application No. 2020156354" with English translation thereof, dated Mar. 1, 2022, p. 1-p. 8.
"Office Action of U.S. Co-Pending Application, U.S. Appl. No. 16/744,182", dated Jul. 19, 2022, pp. 1-33.
"Office Action of U.S. Co-Pending Application, U.S. Appl. No. 16/744,186", dated Jul. 19, 2022, pp. 1-32.
"Office Action of U.S. Co-Pending Application, U.S. Appl. No. 16/744,190", dated Jul. 19, 2022, pp. 1-39.
"Office Action of Europe Related Application No. 18835377.5", dated Jan. 18, 2023, pp. 1-6.
"Office Action of Europe Related Application No. 18835495.5", dated Jan. 20, 2023, pp. 1-4.
"Office Action of Europe Counterpart Application No. 21154040.6", dated Jan. 24, 2023, pp. 1-4.

(56) References Cited

OTHER PUBLICATIONS

Office Action of U.S. Appl. No. 16/744,182, dated Jan. 23, 2023, pp. 1-22.
Office Action of U.S. Appl. No. 16/744,186, dated Jan. 23, 2023, pp. 1-24.
Office Action of U.S. Appl. No. 16/744,190, dated Jan. 23, 2023, pp. 1-26.
"Office Action of co-pending U.S. Appl. No. 16/744,182", dated Jun. 27, 2023, pp. 1-18.
"Office Action of co-pending U.S. Appl. No. 16/744,186", dated Jun. 27, 2023, pp. 1-19.
"Office Action of co-pending U.S. Appl. No. 16/744,190", dated Jun. 27, 2023, pp. 1-22.

* cited by examiner

FIG. 22
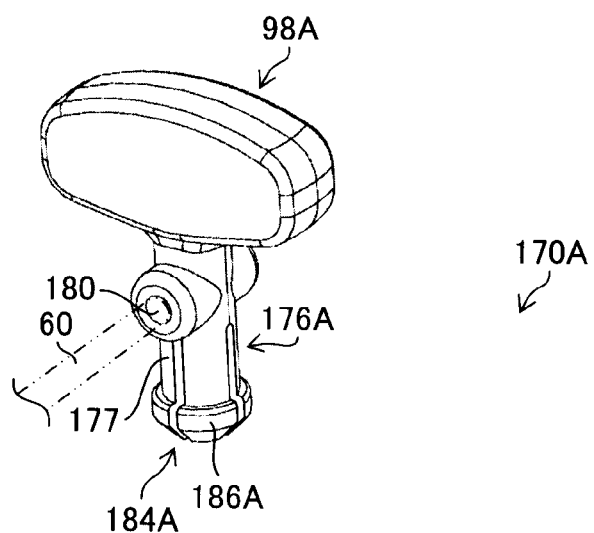
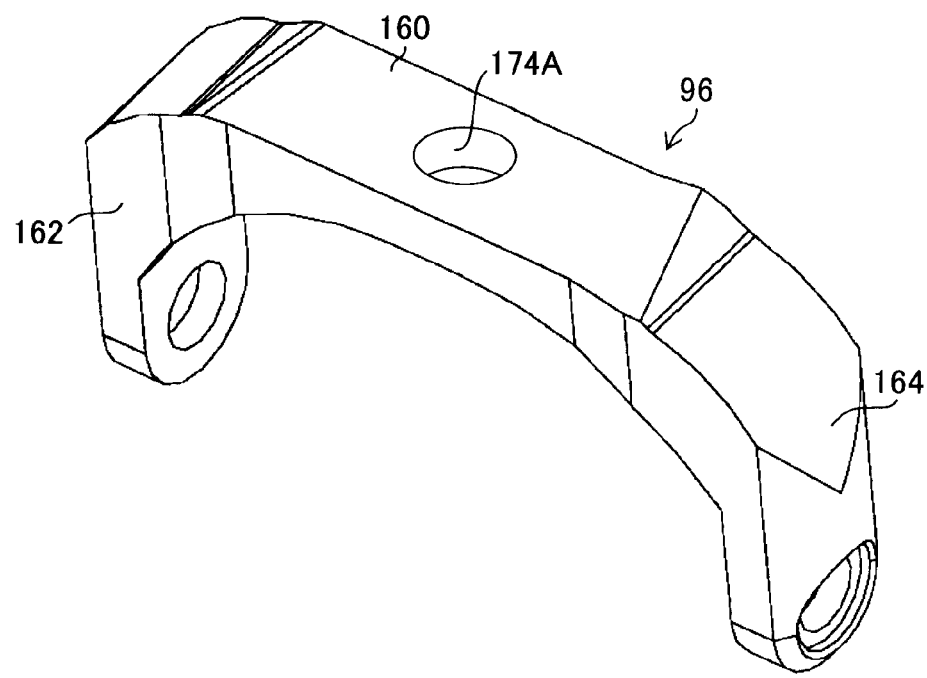

FIG. 27
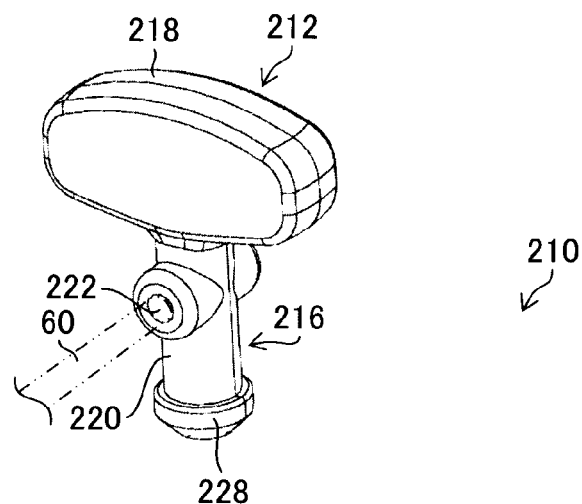
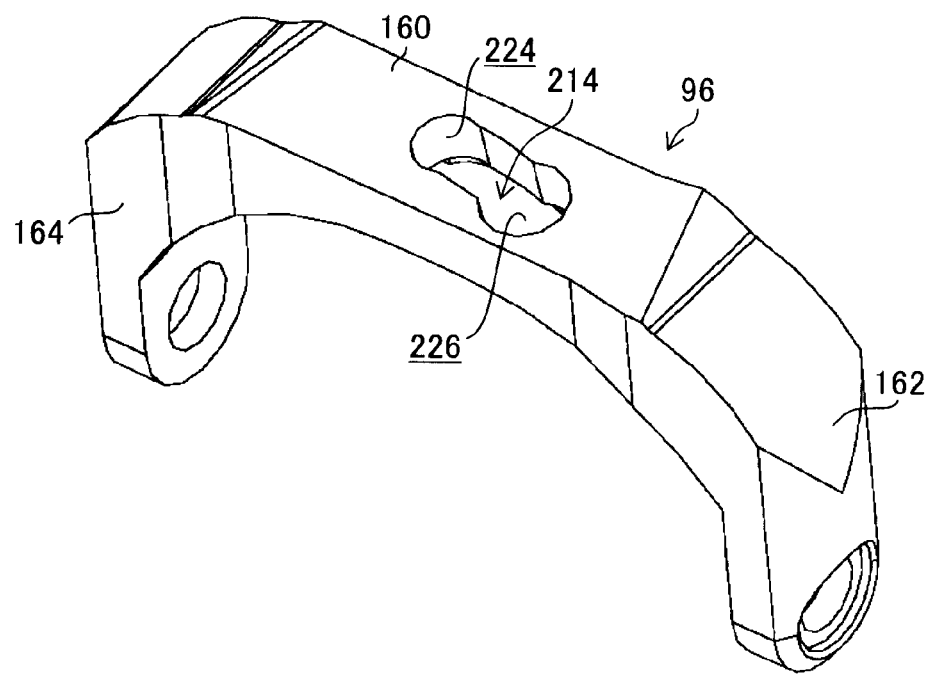

FIG. 30
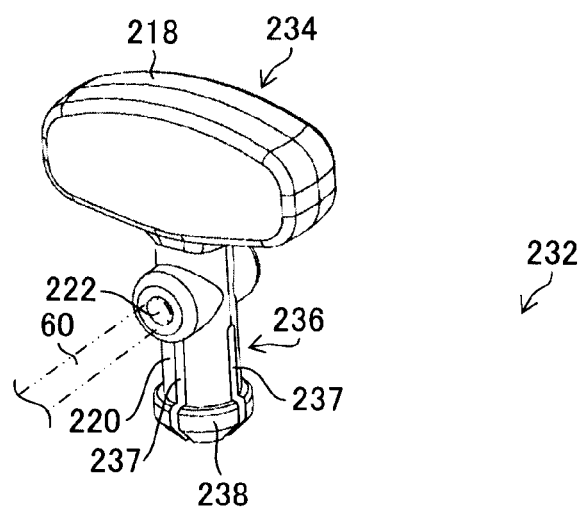
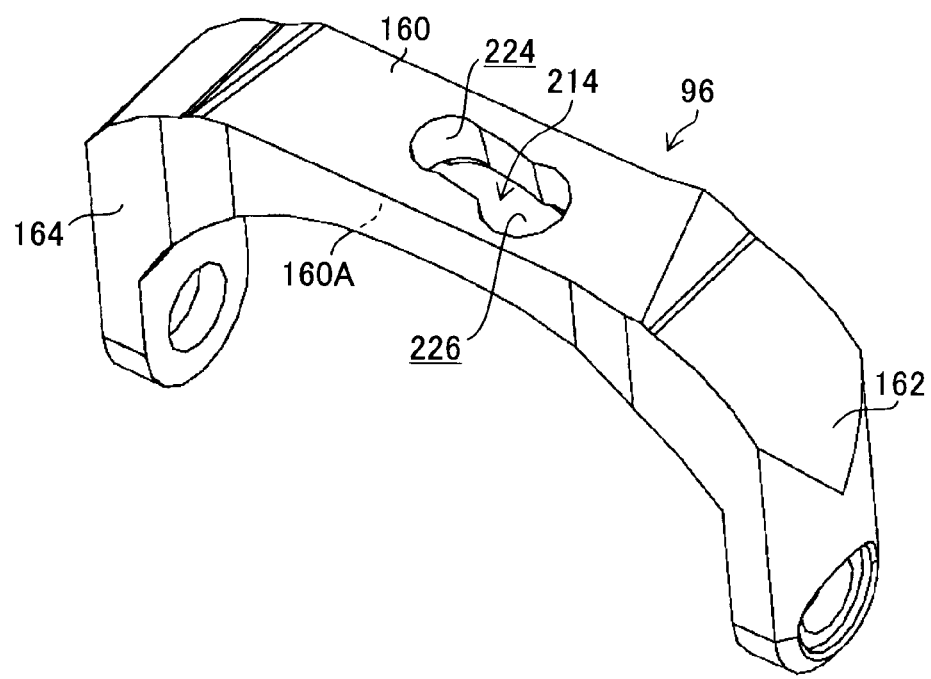

ENDOSCOPE

CROSS-REFERENCE TO RELATED APPLICATIONS

The present application is a Continuation of PCT International Application No. PCT/JP2018/022362 filed on Jun. 12, 2018 claiming priority under 35 U.S.C. § 119(a) to Japanese Patent Application No. 2017-139140 filed on Jul. 18, 2017. Each of the above applications is hereby expressly incorporated by reference, in its entirety, into the present application.

BACKGROUND OF THE INVENTION

1. Field of the Invention

The present invention relates to endoscopes, and more particularly relates to an endoscope including a treatment tool erecting base that changes a lead-out direction of a treatment tool, at a distal end part of an insertion section.

2. Description of the Related Art

In an endoscope, one of various treatment tools is led in from a treatment tool lead-in port provided in a hand operation section (hereinafter, referred to as "operation section"), and the treatment tool is led out from a treatment tool lead-out port opening in a distal end member of an insertion section to the outside to be used for a treatment. For example, a treatment tool, such as forceps or a contrast agent tube, is used for a duodenum endoscope, and a treatment tool, such as a puncture needle, is used for an ultrasonic endoscope. With such a treatment tool, to provide a treatment at a desirable position in a subject, a lead-out direction of the treatment tool that is led out from the treatment tool lead-out port needs to be changed. Hence, the distal end member is provided with a treatment tool erecting base (hereinafter, referred to as "erecting base"), and the endoscope is provided with a treatment tool erecting mechanism that changes the posture of the erecting base between an erecting position and a lying position.

For the treatment tool erecting mechanism, a wire pulling mechanism is known (see JP1994-315458A (JP-H6-315458A)), in which a distal end portion of a wire (also referred to as forceps erecting wire) is directly attached to an erecting base. The mechanism couples the proximal end side of the wire to an erecting operation lever (also referred to as forceps erecting lever) included in an operation section, operates the wire to be pushed/pulled by using the erecting operation lever to rotate the erecting base around a rotation shaft, and hence changes the posture of the erecting base between an erecting position and a lying position.

More specifically, the operation section of JP1994-315458A (JP-H6-315458A) is provided with a grip part for holding the operation section with a hand, and an angle knob. The operation section has a wire opening portion below the grip part, and a drive shaft opening portion in the grip part. The proximal end of the wire is led out from the wire opening portion. The distal end of the drive shaft that is moved by the forceps erecting lever is led out from the drive shaft opening portion. The distal end of the drive shaft and the proximal end of the wire are removably coupled to a connecting tool. A protection cover that covers the connecting tool is provided on the operation section in an attachable/detachable manner.

When an endoscope is used for one of various inspections or one of various treatments, liquid in a body cavity adheres to the distal end member of the insertion section including the erecting base and to a guide pipe through which the wire is inserted. The endoscope after use is subjected to washing and disinfection processing using a washing solution and a disinfectant. At this time, since the guide pipe has a small diameter and the wire is inserted through the inside of the guide pipe, washing is troublesome.

Owing to this, in the endoscope of JP1994-315458A (JP-H6-315458A)), the cover covering the distal end member of the insertion section, the erecting base, and the wire are provided in an attachable/detachable manner; the cover, the erecting base, and the wire are removed; and the distal end member of the insertion section and the guide pipe of the wire are washed.

Moreover, EP1759626B discloses an endoscope in which the proximal end of a cable cord is led out from the proximal end of a control handle, and the proximal end of the cable cord is connected to a collet. The collet is fastened to a nut and moves in the front-rear direction by an operation lever.

SUMMARY OF THE INVENTION

However, since the endoscope of JP1994-315458A (JP-H6-315458A) is configured such that the connecting tool serving as the erecting operation mechanism is housed in the narrow area in the operation section, the attachment/detachment operation of the proximal end of the wire to/from the erecting operation mechanism is troublesome.

In addition, with the endoscope of JP1994-315458A (JP-H6-315458A), the operation section is increased in size by the amount that the connecting tool of the erecting operation mechanism is housed in the operation section.

With the endoscope of EP1759626B, the cable cord is led out to the outside of the control handle, and the distal end of the cable cord is mounted at the collet and the nut in an attachable/detachable manner. However, the attachment/detachment operation is troublesome. When the cable cord meanders in a casing during an operation, a rotatable part may be no longer operated. Even when the cable cord operates the rotatable part in a lying direction, the cable cord may meander and may not lie to a desirable position, and insertion performance may not be sufficient when the distal end part of the endoscope is inserted. Moreover, when the cable cord is inserted through the casing, the cable cord may meander, and an insertion work may not be easily performed.

The present invention is made in light of the situations, and it is an object of the invention to provide an endoscope in which an attachment/detachment operation of the proximal end of a wire is easily performed to/from an erecting operation mechanism, the wire can be prevented from meandering in a channel, a treatment tool erecting base can lie to a requested position, and operability and insertion performance are at high levels.

To attain the object of the present invention, an endoscope according to the present invention includes an operation section provided with an operating member; an insertion section that is provided on a distal end side of the operation section and that is inserted into a subject; a treatment tool erecting base provided at a distal end part of the insertion section; a movable member that is arranged to be exposed to outside of the operation section and that moves in association with an operation of the operating member; a proximal end opening provided in the operation section; a distal end opening provided in the distal end part; an erecting operation wire channel that is provided in the insertion section and that causes the proximal end opening to communicate with the distal end opening; an erecting operation wire that is inserted through the erecting operation wire channel, that has a distal end side which is arranged outside the distal end opening and which is coupled to the treatment tool erecting base, that has a proximal end side which is arranged outside the proximal end opening and which is coupled to the movable member, and that is pushed or pulled in accordance with a movement of the movable member to move the treatment tool erecting base; and an attachment member that is provided at a proximal end of the erecting operation wire and that is engaged with the movable member in an attachable/detachable manner by a one-touch operation. The erecting operation wire has a flexible long wire body, and a gap filling member that is arranged at at least a portion in an axial direction of the wire body and that is formed to have a diameter larger than an outside diameter of the wire body and smaller than an inside diameter of the erecting operation wire channel.

According to an aspect of the present invention, preferably, the gap filling member functions as a meandering prevention member that prevents the wire body from meandering by coming into contact with an inner surface of the erecting operation wire channel.

According to an aspect of the present invention, preferably, the gap filling member functions as a backflow prevention member that prevents a fluid from flowing backward from the distal end opening to the proximal end opening in the erecting operation wire channel.

According to an aspect of the present invention, preferably, a plurality of the gap filling members are provided at mutually different positions in the axial direction of the wire body.

According to an aspect of the present invention, preferably, the gap filling member is a columnar or spherical expansion portion provided at the wire body.

According to an aspect of the present invention, preferably, the gap filling members is a long outer layer member that is disposed on an outer periphery side of the wire body and that extends in the axial direction of the wire body.

According to an aspect of the present invention, preferably, the outer layer member is a tubular body through which the wire body is inserted to allow the wire body to freely advance/retract therethrough.

According to an aspect of the present invention, preferably, the wire body has a first position regulation portion that regulates a position of the tubular body in the axial direction of the wire body.

According to an aspect of the present invention, preferably, the tubular body has a second position regulation portion that regulates a position of the tubular body in a longitudinal direction of the erecting operation wire channel.

According to an aspect of the present invention, preferably, an engagement hole is provided in one of the movable member and the attachment member, and an engagement portion that is engaged with the engagement hole in an attachable/detachable manner is provided at the other one.

According to an aspect of the present invention, preferably, the engagement portion is provided with an elastic deformation portion that is elastically deformed and engaged with the engagement hole.

According to an aspect of the present invention, preferably, a pair of claw portions are formed at the elastic deformation portion, the pair of claw portions being elastically deformable and configured to be latched to an edge portion of the engagement hole, the pair of claw portions being displaced in directions to move toward each other by elastic deformation when the engagement portion is engaged with or disengaged from the engagement hole.

According to an aspect of the present invention, preferably, the engagement hole has a small width portion having a first width, and a large width portion having a second width that is larger than the first width; and the engagement portion has a shaft portion having an outside diameter that is smaller than the first width, and a large diameter portion provided at a distal end of the shaft portion and having an outside diameter that is larger than the first width and smaller than the second width.

According to an aspect of the present invention, preferably, one of the movable member and the attachment member is provided with a cylindrical body extending in a direction perpendicular to an axial direction of the erecting operation wire, and the other one is provided with a ring-shaped body that is rotatably engaged with an outer periphery of the cylindrical body; and the endoscope includes a rotation restriction stopper that restricts relative rotations of the cylindrical body and the ring-shaped body.

According to an aspect of the present invention, preferably, the endoscope includes an engagement member provided at a distal end of the erecting operation wire; and a housing groove that is provided in the treatment tool erecting base and that is engaged with the engagement member in an engageable/disengageable manner.

According to an aspect of the present invention, preferably, the movable member is rotatably provided while a direction perpendicular to an axial direction of the erecting operation wire serves as a rotation axis.

According to an aspect of the present invention, preferably, the operating member is an operating member rotatably supported by the operation section; and the endoscope includes a first conversion mechanism that converts a rotational motion of the operating member into a linear motion, a drive member that is linearly driven by the first conversion mechanism, and a second conversion mechanism that converts a linear motion of the drive member into a rotational motion to rotate the movable member.

According to an aspect of the present invention, preferably, the second conversion mechanism includes a speed reduction mechanism.

With the present invention, the endoscope can be provided in which the attachment/detachment operation of the proximal end of the wire is easily performed to/from the erecting operation mechanism, the wire can be prevented from meandering in the channel, the treatment tool erecting base can lie to the requested position, and the operability and insertion performance are at high levels.

BRIEF DESCRIPTION OF THE DRAWINGS

FIG. 22 is an explanatory diagram illustrating a modification of the coupling structure according to the first embodiment;

FIG. 27 is an assembly perspective view of the coupling structure illustrated in FIG. 26;

FIG. 30 is an assembly perspective view of a coupling structure according to a third embodiment;

DESCRIPTION OF THE PREFERRED EMBODIMENTS

Endoscopes according to preferred embodiments of the present invention are described in detail below with reference to the accompanying drawings.

Figure 1:
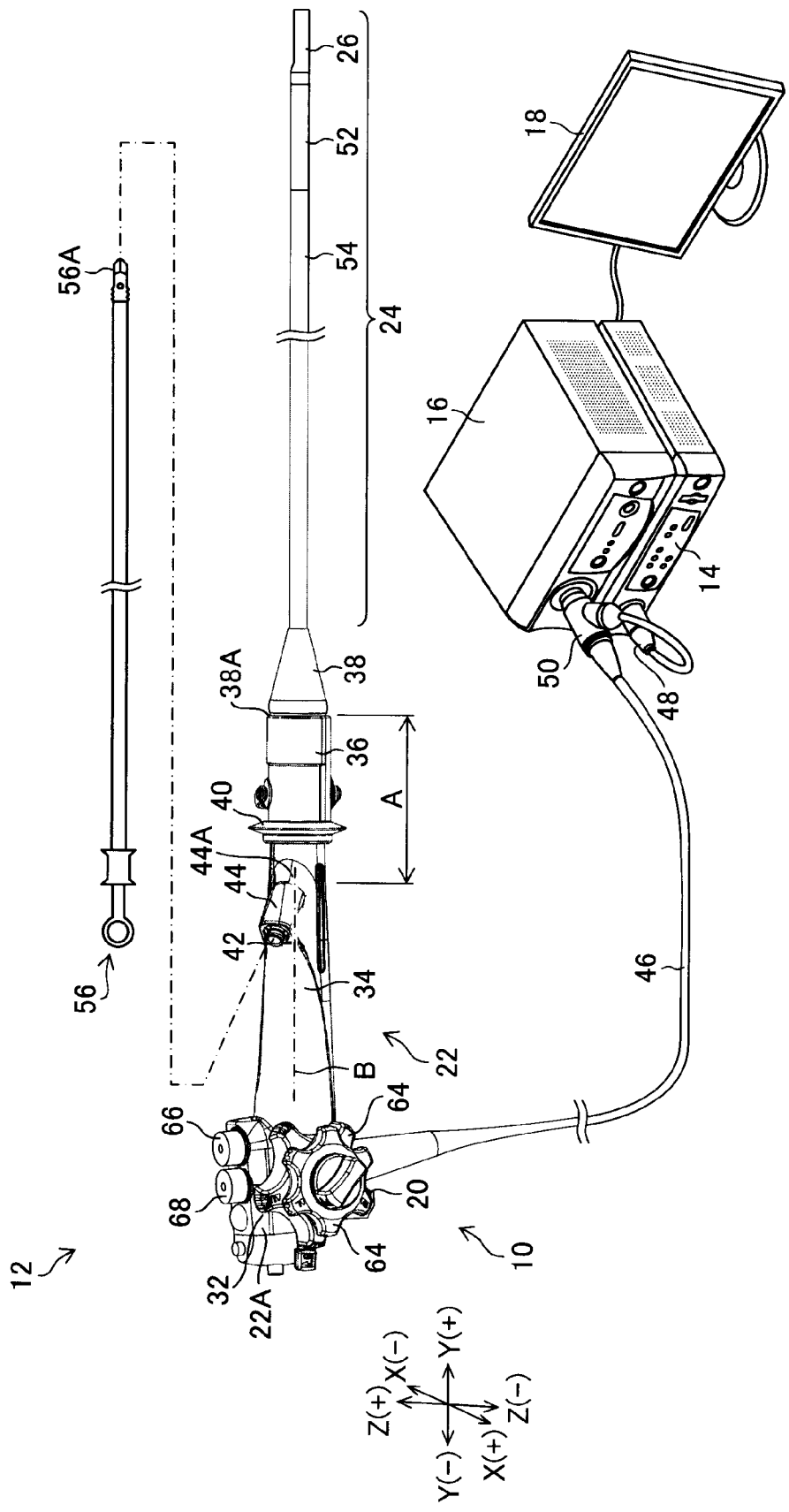
FIG. 1 is a configuration diagram of an endoscope system including an endoscope according to an embodiment.

FIG. 1 is a configuration diagram of an endoscope system 12 including an endoscope 10 according to an embodiment of the present invention. The endoscope system 12 includes an endoscope 10, a processor device 14, a light source device 16, and a display 18. FIG. 1 also illustrates a treatment tool 56 that is used in the endoscope system 12.

The endoscope 10 includes an operation section 22 including an erecting operation lever 20 that serves as an operating member, and an insertion section 24 provided on the distal end side of the operation section 22.

Figure 2:
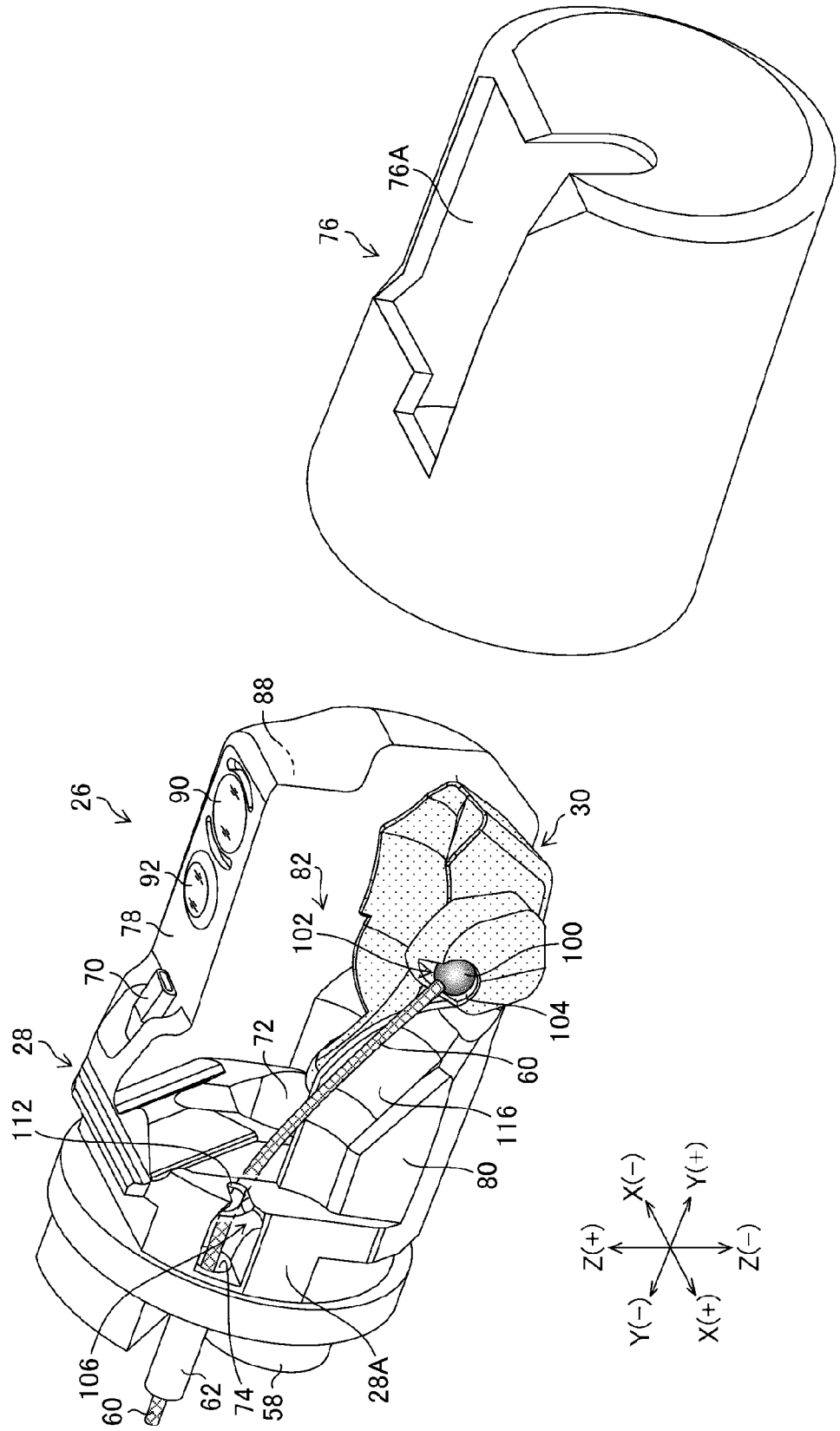
FIG. 2 is a perspective view of a distal end member when an erecting base is located at a lying position.
Figure 3:
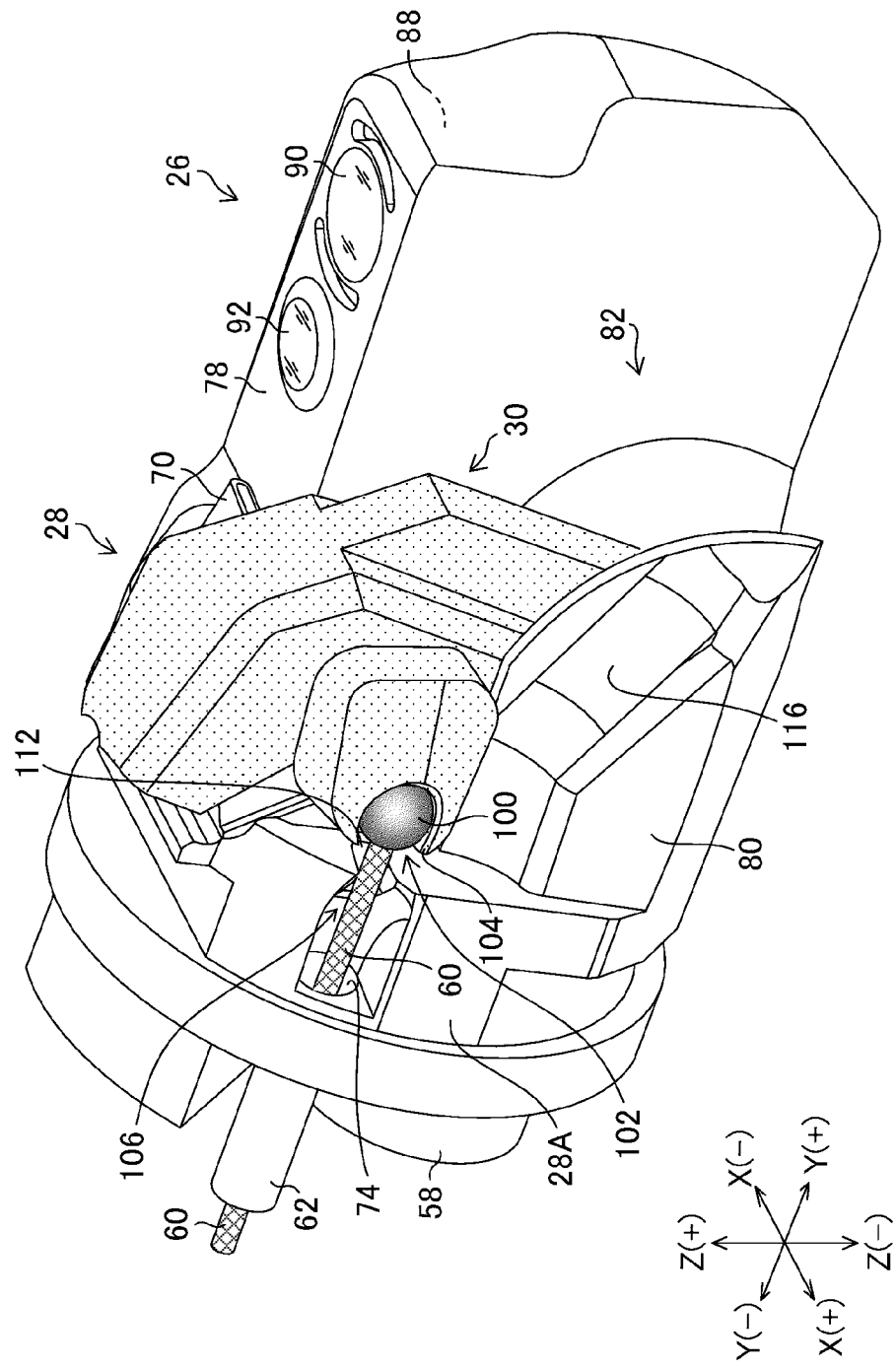
FIG. 3 is a perspective view of the distal end member when the erecting base is located at an erecting position.

Referring to perspective views in FIGS. 2 and 3 illustrating the configuration of a distal end part 26 of the insertion section 24, a distal end member 28 is provided at the distal end part 26 of the insertion section 24, and an erecting base 30 (described later) is attached to the distal end member 28. FIG. 2 is a perspective view of the distal end member 28 when the erecting base 30 is located at a lying position. FIG. 3 is a perspective view of the distal end member 28 when the erecting base 30 is located at an erecting position.

In the following description, an upward direction indicates a Z(+) direction in FIGS. 1 and 2, and a downward direction indicates a Z(−) direction in FIGS. 1 and 2. Moreover, a rightward direction indicates an X(+) direction in FIG. 2, and a leftward direction indicates an X(−) direction in FIG. 2. Furthermore, a Y(+) direction in FIGS. 1 and 2 indicates a distal end side direction of the distal end member 28, and a Y(−) direction in FIGS. 1 and 2 indicates a proximal end side direction of the distal end member 28.

Referring back to FIG. 1, the operation section 22 has an operation section main body 32 provided with the erecting operation lever 20, a holding part 34 connected to the operation section main body 32, and an extension part 36 extending from the holding part 34 toward the distal end side. A proximal end portion of the insertion section 24 is provided on the distal end side of the extension part 36 via a break prevention pipe 38. The holding part 34 is a part that is held by an operator during an operation of the endoscope 10.

The extension part 36 is a part in a non-holding region that is extended from a distal end portion of the holding part 34 toward the distal end side to provide part of components of a movable member 96 (described later, see FIG. 6) and an erecting operation mechanism 120 (described later, see FIGS. 9 and 10) on the extension part 36. Specifically, a region A extending from a distal end portion 44A of a protruding mount portion 44 of a treatment tool lead-in port 42 provided in the holding part 34 to a proximal end portion 38A of the break prevention pipe 38 corresponds to the extension part 36. An extension-pipe-shaped flange 40 is provided in the region of the extension part 36.

The operation section main body 32 of the operation section 22 includes a universal cord 46. A light source connector 50 is provided on the distal end side of the universal cord 46. An electric connector 48 branches out from the light source connector 50. The electric connector 48 is connected to the processor device 14, and the light source connector 50 is connected to the light source device 16.

The insertion section 24 includes the distal end part 26, a bending part 52, and a soft part 54 that are coupled from the distal end side toward the proximal end side.

The insertion section 24 incorporates the following contents. In particular, the contents include, for example, a treatment tool channel 58 that guides a distal end portion 56A of the treatment tool 56 in FIG. 1 to the distal end member 28 in FIG. 2; an erecting operation wire 60 (hereinafter, referred to as wire 60) for performing an operation of changing a lead-out direction of the distal end portion 56A of the treatment tool 56 led out from the distal end member 28; an erecting operation wire channel 62 (hereinafter, referred to as wire channel 62) that guides a distal end portion of the wire 60 to the distal end member 28; a light guide (not illustrated) that guides illumination light supplied from the light source device 16 in FIG. 1 to the distal end member 28 in FIG. 2; an air/water supply tube (not illustrated); an angle wire (not illustrated); and a signal cable (not illustrated).

Referring back to FIG. 1, the operation section 22 is formed in a substantially cylindrical shape as a whole and has a cylinder axis B along the Y(+)-Y(−) direction. A pair of angle knobs 64 that perform an operation of bending the bending part 52 are arranged at a side surface 22A on one side with respect to a section extending in the up-down direction and including the cylinder axis B of the operation section 22. The pair of angle knobs 64 are coaxially rotatably provided.

The bending part 52 has a structure in which a plurality of angle rings (not illustrated) are mutually rotatably coupled. The bending part 52 is configured such that the outer periphery of the structure is covered with a tubular mesh body braided using metal wires, and the outer peripheral surface of the mesh body is covered with a tubular outer sheath made of rubber. For example, four angle wires (not illustrated) are disposed to extend from the thus configured bending part 52 to the angle knobs 64. An operation of pushing/pulling the angle wires is performed by an operation of rotating the angle knobs 64 to bend the bending part 52 upward, downward, leftward, and rightward.

Moreover, on the operation section main body 32 of the operation section 22, an air/water supply button 66 and a suction button 68 are arranged side by side. By operating the air/water supply button 66, the air and water can be ejected from an air/water supply nozzle 70 provided in the distal end member 28 in FIG. 2. By operating the suction button 68 in FIG. 1, body fluids such as blood can be sucked from a suction port that also serves as a treatment tool lead-out port 72 provided in the distal end member 28 in FIG. 2.

Furthermore, a treatment tool lead-in port 42 is provided in the holding part 34 of the operation section 22 in FIG. 1. The treatment tool 56 is led in to the treatment tool lead-in port 42. The treatment tool 56 led in from the treatment tool lead-in port 42 while the distal end portion 56A is at the head is inserted through the treatment tool channel 58 in FIG. 2 inserted through the insertion section 24, and is led out to the outside from the treatment tool lead-out port 72 provided in the distal end member 28.

The erecting operation lever 20 is rotatably provided at the one side surface 22A of the operation section 22 in FIG. 1 in a manner coaxial with the angle knobs 64. The erecting operation lever 20 is rotationally operated by a hand of the operator who holds the holding part 34. When the erecting operation lever 20 is rotationally operated, the wire 60 in FIG. 2 is pushed/pulled by an erecting operation mechanism 120 (see FIGS. 9 and 10) that moves in association with the rotational operation of the erecting operation lever 20, and the posture of the erecting base 30 coupled to the distal end side of the wire 60 is changed between an erecting position in FIG. 3 and a lying position in FIG. 2. The above-described erecting operation mechanism 120 will be described later.

The soft part 54 illustrated in FIG. 1 has a helical pipe (not illustrated) formed by winding a thin elastic strip-shaped plate made of metal in a helical form. The outside of the helical pipe of the soft part 54 is covered with a tubular mesh body braided using metal wires. The outer peripheral surface of the mesh body is covered with a tubular outer sheath made of resin.

The endoscope 10 according to the thus configured embodiment is a side-view endoscope used as a duodenum endoscope. The insertion section 24 is inserted into a subject via the oral cavity. The insertion section 24 is inserted from the esophagus via the stomach to the duodenum, and, for example, a treatment, such as a predetermined inspection or a predetermined medical care, is performed.

In the embodiment, biopsy forceps serve as an example of the treatment tool 56, the biopsy forceps having a cup capable of collecting a living tissue at the distal end portion 56A. However, it is not limited thereto. For example, a treatment tool, such as a contrast agent tube or an endoscopic sphincterotomy (EST) knife, is used as another treatment tool.

Next, the distal end part 26 of the insertion section 24 is described.

Referring to FIG. 2, the distal end part 26 of the insertion section 24 is configured of the distal end member 28, and a cap 76 that is mounted on the distal end member 28 in an attachable/detachable manner. The cap 76 has a substantially tubular shape whose distal end side is sealed. A substantially rectangular opening window 76A is formed in part of the outer peripheral surface of the cap 76. When the cap 76 is mounted on the distal end member 28, the opening window 76A of the cap 76 communicates with the treatment tool lead-out port 72 of the distal end member 28. Thus, the distal end portion 56A of the treatment tool 56 led out from the treatment tool lead-out port 72 is led out to the outside from the opening window 76A.

The cap 76 is made of an elastic material, for example, a rubber material, such as fluorocarbon rubber or silicon rubber; or a resin material such as polysulfone. An engagement portion (not illustrated) is provided on the proximal end side of the cap 76. The engagement portion is engaged with a groove (not illustrated) formed in the distal end member 28. By engaging the engagement portion with the groove of the distal end member 28, the cap 76 is mounted on the distal end member 28. When the treatment with the endoscope 10 is ended, the cap 76 is removed from the distal end member 28, and washed and disinfected, or discarded as a disposable.

The distal end member 28 is made of a corrosion-resistant metal material. Moreover, in the distal end member 28, a partition wall 78 protruding toward the distal end side and a partition wall 80 opposite to the partition wall 78 are integrally provided. An erecting base housing chamber 82 that houses the erecting base 30 is formed between the partition wall 78 and the partition wall 80. The treatment tool lead-out port 72 that leads out the treatment tool 56 to the outside is formed on the proximal end side of the erecting base housing chamber 82. A distal end portion of the treatment tool channel 58 is connected to the treatment tool lead-out port 72.

The treatment tool channel 58 is inserted through the inside of the insertion section 24 in FIG. 1. A proximal end portion of the treatment tool channel 58 is connected to a distal end pipe 202 of a branch pipe 200 (see FIG. 10) provided in the operation section 22.

The branch pipe 200 has a known structure. A proximal end portion of the branch pipe 200 is branched into two pipe lines 204 and 206. The treatment tool lead-in port 42 is formed at the proximal end of the one pipe line 204. The distal end portion 56A of the treatment tool 56 led in from the treatment tool lead-in port 42 to the treatment tool channel 58 via the pipe line 204 is inserted through the treatment tool channel 58, and is led out from the treatment tool lead-out port 72 in FIG. 2 to the erecting base housing chamber 82. The lead-out direction of the distal end portion 56A of the treatment tool 56 led out to the erecting base housing chamber 82 is changed in accordance with the posture between the erecting position and the lying position of the erecting base 30 arranged in the erecting base housing chamber 82. Moreover, the distal end of a suction pipe 208 for sucking body fluids such as blood is connected to the proximal end of the other pipe line 206 of the branch pipe 200 illustrated in FIG. 10.

Figure 4:
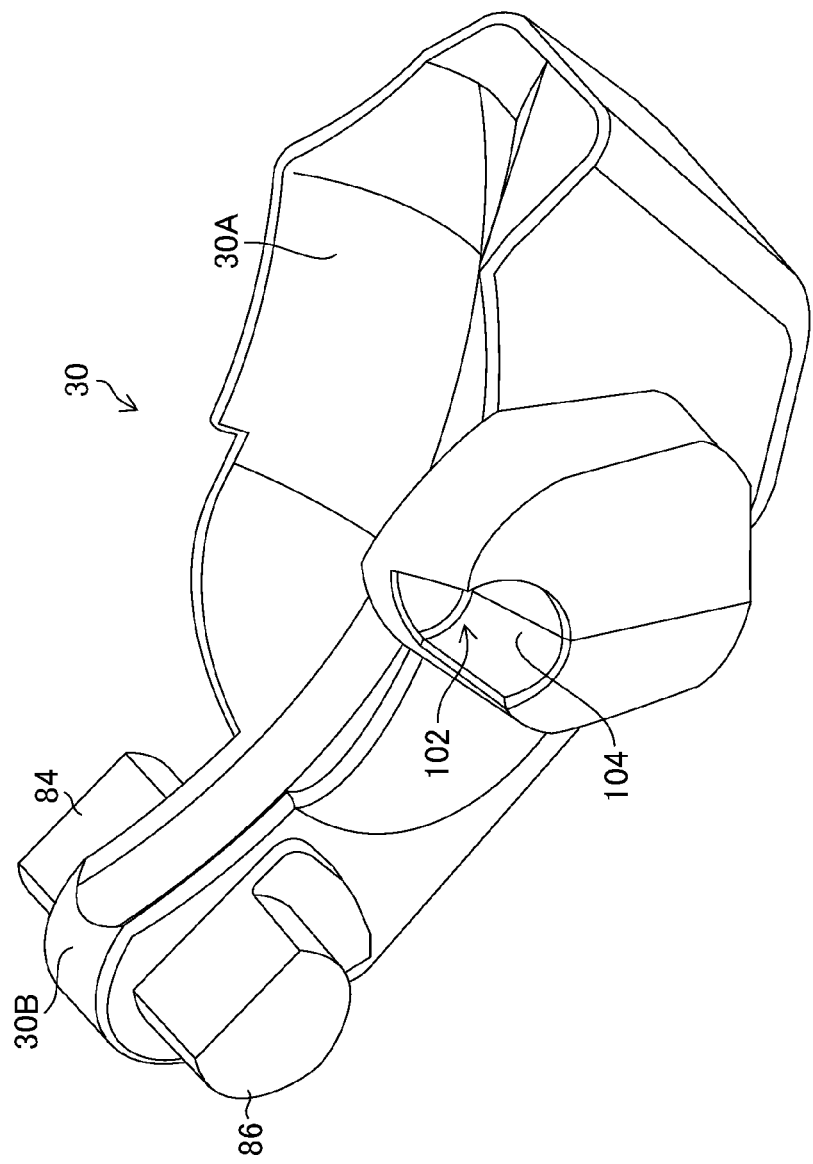
FIG. 4 is an enlarged perspective view of the erecting base.

FIG. 4 is an enlarged perspective view of the erecting base 30. Referring to FIG. 4, a guide surface 30A is included in an upper surface of the erecting base 30. Along the guide surface 30A, the distal end portion 56A of the treatment tool 56 in FIG. 1 is led out to the outside from the opening window 76A of the cap 76 in FIG. 2.

Referring to FIG. 4, the erecting base 30 includes rotation shafts 84 and 86 on both side surfaces of a base portion 30B of the erecting base 30. The axial direction of the rotation shafts 84 and 86 is set in the X(+)-X(−) direction in FIG. 2 when the erecting base 30 is attached to the distal end member 28.

Figure 5:
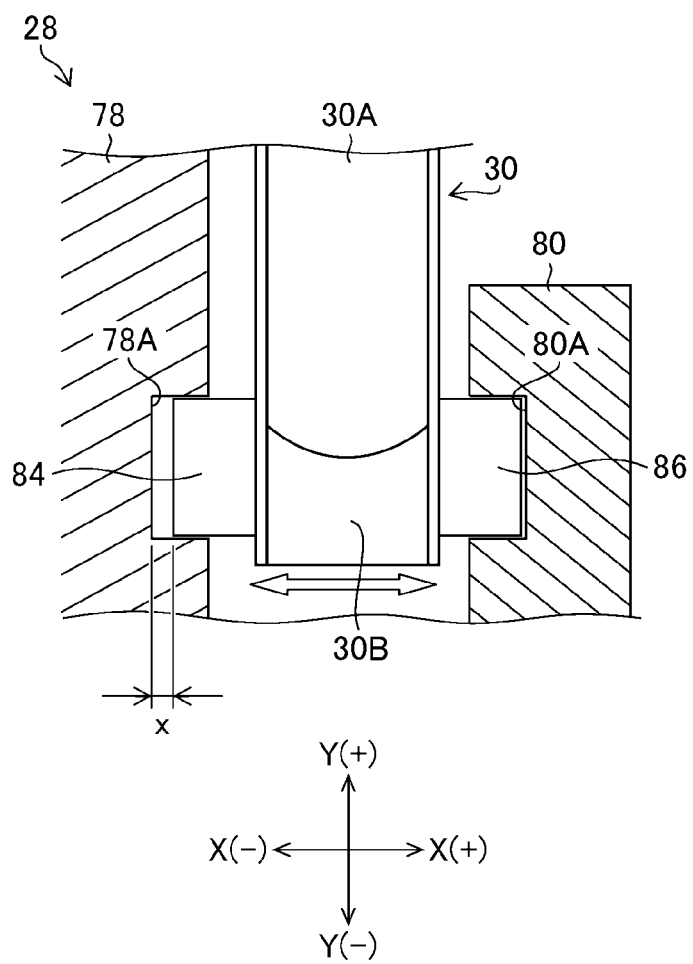
FIG. 5 is a main-part sectional view illustrating an attachment structure of the erecting base to the distal end member.

FIG. 5 is a main-part sectional view illustrating an attachment structure of the erecting base 30 to the distal end member 28. Referring to FIG. 5, the axes of the rotation shafts 84 and 86 are coaxially arranged via the base portion 30B of the erecting base 30. The rotation shaft 84 is rotatably fitted to a recessed bearing portion 78A of the partition wall 78. The rotation shaft 86 is rotatably fitted to a recessed bearing portion 80A of the partition wall 80. Moreover, the rotation shafts 84 and 86 are mounted at the bearing portions 78A and 80A respectively with a predetermined backlash amount x in the axial direction of the rotation shafts 84 and 86. When the rotation shafts 84 and 86 are moved to one side by using the backlash amount x, a portion of one bearing portion of the bearing portions 78A and 80A is exposed, and a brush can be easily inserted to the exposed portion, thereby increasing washing efficiency of the bearing portions 78A and 80A.

Referring to FIGS. 2 and 3, an optical system housing chamber 88 is included in the partition wall 78. An illumination window 90 and an observation window 92 are adjacently disposed at an upper portion of the optical system housing chamber 88. In addition, the air/water supply nozzle 70 directed to the observation window 92 is provided at the distal end member 28. The air/water supply nozzle 70 is connected to an air/water supply device (not illustrated) via an air/water supply tube (not illustrated) inserted through the insertion section 24. By operating the air/water supply button 66 of the operation section 22 illustrated in FIG. 1, the air or water is ejected from the air/water supply nozzle 70 toward the observation window 92. Accordingly, the observation window 92 is washed.

An illumination unit (not illustrated) and an imaging unit (not illustrated) are housed in the optical system housing chamber 88. The illumination unit includes an illumination lens (not illustrated) disposed inside the illumination window 90 and a light guide (not illustrated) arranged such that a distal end surface of the light guide faces the illumination lens. The light guide is disposed to extend from the insertion section 24 via the operation section 22 to the universal cord 46 of the endoscope 10, and the proximal end thereof is connected to the light source device 16 via the light source connector 50. Thus, the irradiation light from the light source device 16 is transmitted through the light guide and is emitted from the illumination window 90 to the outside.

The above-described imaging unit includes an imaging optical system (not illustrated) disposed inside the observation window 92 and an imaging element (not illustrated) of a complementary metal oxide semiconductor (CMOS) or a charge coupled device (CCD). The imaging element is connected to the processor device 14 via a signal cable (not illustrated) inserted through the insertion section 24 in FIG. 1. An imaging signal of a subject image obtained by the imaging unit is output to the processor device 14 via the signal cable, undergoes image processing, and then is displayed as a subject image on the display 18.

Next, an engagement structure for engaging the distal end of the wire 60 with the erecting base 30 in an engageable/disengageable manner is described.

Figure 6:
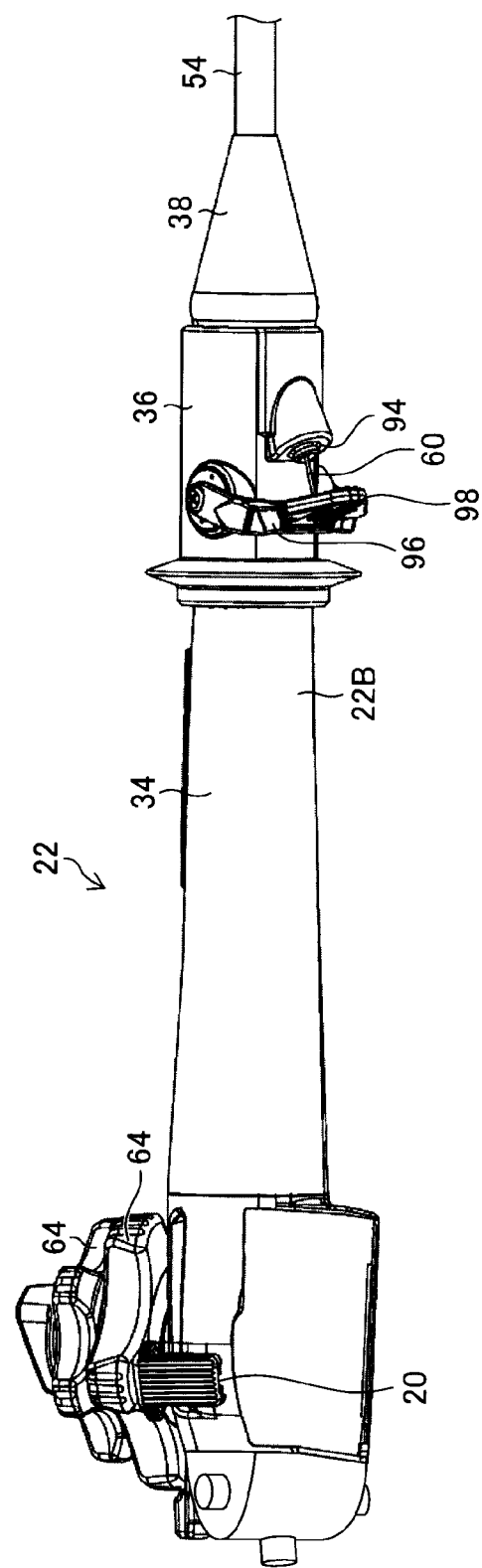
FIG. 6 is a perspective view illustrating the other side surface opposite to one side surface of an operation section illustrated in FIG. 1.

FIG. 6 is a perspective view of the operation section 22, and is a perspective view illustrating the other side surface 22B opposite to the one side surface 22A of the operation section 22 illustrated in FIG. 1.

Referring to FIG. 6, the lead-in port 94 that configures a proximal end opening is provided in the extension part 36 of the operation section 22. An attachment member 98 is provided at the proximal end of the wire 60 arranged at the outside from the lead-in port 94. The attachment member 98 is mounted at an engagement hole (described later) of the movable member 96 in an attachable/detachable manner.

The operation section 22 is provided with the movable member 96. The movable member 96 is arranged to be exposed to the outside of the operation section 22. The movable member 96 moves in association with the operation of the erecting operation lever 20 by the erecting operation mechanism 120 (described later). In the embodiment, the movable member 96 is rotatably arranged at the other side surface 22B opposite to the one side surface 22A provided with the angle knobs 64. However, the arrangement position of the movable member 96 with respect to the operation section 22 is not limited, and may be rotatably arranged at a predetermined position of the operation section 22. The movable member 96 is a driven lever that rotates in association with the rotational operation of the erecting operation lever 20.

The erecting operation mechanism 120 is arranged inside the operation section 22. The erecting operation mechanism 120 moves the movable member 96 in association with the operation of the erecting operation lever 20. Thus, when the erecting operation lever 20 is operated, the movable member 96 moves via the erecting operation mechanism 120, and the wire 60 (see FIG. 2) coupled to the movable member 96 is pushed/pulled. The erecting operation mechanism 120 will be described later.

Next, an engagement structure for engaging the distal end of the wire 60 with the erecting base 30 in an engageable/disengageable manner is described.

Referring back to FIGS. 2 and 3, the distal end of the wire 60 is provided with an engagement member 100. Moreover, the erecting base 30 is provided with a housing groove 102 having an opening 104 formed on the side in the X(+) direction. The engagement member 100 is engaged with the housing groove 102 in an engageable/disengageable manner. Accordingly, by housing the engagement member 100 provided at the distal end of the wire 60 in the housing groove 102 via the opening 104, the distal end of the wire 60 is coupled to the erecting base 30.

In the embodiment, the engagement member 100 is a sphere, and the housing groove 102 is a spherical-surface-shaped concave portion that houses the spherical engagement member 100. The shapes of the engagement member 100 and the housing groove 102 are not limited to the above-described shapes. However, as long as the engagement member 100 is the sphere and the housing groove 102 is the spherical-surface-shaped concave portion, the sliding resistance between the engagement member 100 and the housing groove 102 generated by the pushing/pulling operation of the wire 60 can be decreased. Accordingly, the pushing/pulling operation of the wire 60 can be smoothly performed.

Moreover, the distal end member 28 includes an engagement guide portion 106 connected to the housing groove 102 at the erecting position in FIG. 3. The engagement guide portion 106 includes a function of guiding the engagement member 100 led out from a lead-out port 74 that configures a distal end opening, to the opening 104 of the housing groove 102. The lead-out port 74 is provided in the distal end member 28, and communicates with the lead-in port 94 (see FIG. 6) via the wire channel 62 provided in the insertion section 24.

With the endoscope 10 having such an engagement guide portion 106, when the wire 60 is led in from the lead-in port 94 while the engagement member 100 is at the head, the engagement member 100 is inserted through the wire channel 62 (see FIG. 2) and is led out to the outside from the lead-out port 74. The engagement member 100 is guided by the engagement guide portion 106 toward the opening 104 of the housing groove 102 of the erecting base 30 through the ongoing lead-in operation of the wire 60, and is engaged with the housing groove 102 from the opening 104. Accordingly, with the endoscope 10 according to the embodiment, the engagement member 100 of the wire 60 can be engaged with the housing groove 102 of the erecting base 30 only by the lead-in operation of the wire 60.

Figure 7:
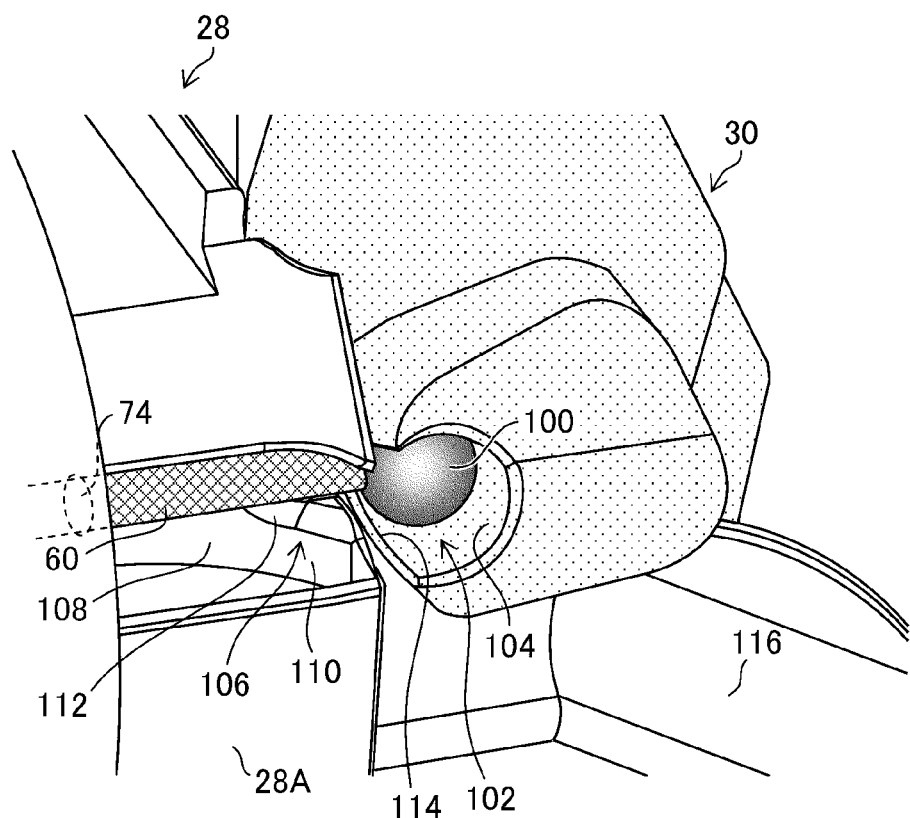
FIG. 7 is an enlarged perspective view when an engagement portion is housed in a housing portion via an engagement guide portion.
Figure 8:
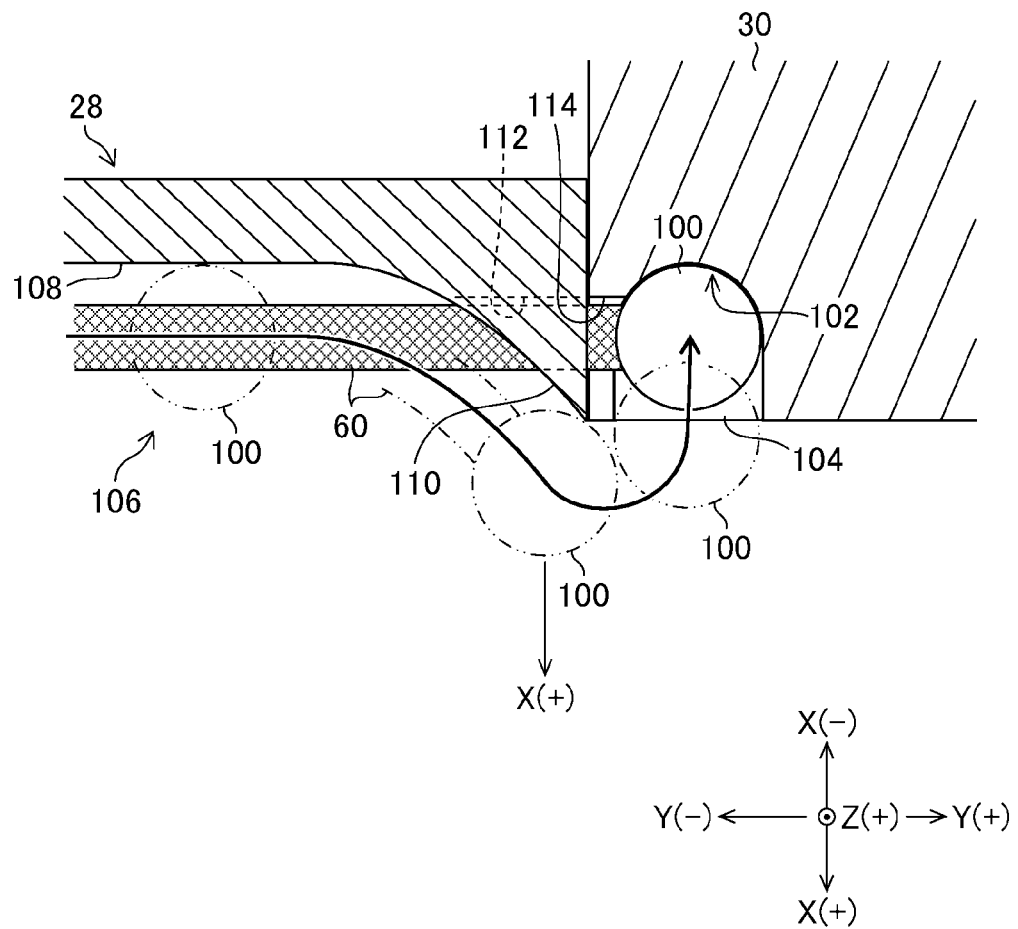
FIG. 8 is a movement explanatory diagram when the engagement portion is guided by the engagement guide portion and housed in the housing portion.

FIG. 7 is an enlarged perspective view when the engagement member 100 is engaged with the housing groove 102 via the engagement guide portion 106. FIG. 8 is an explanatory diagram illustrating a successive movement until the engagement member 100 is guided by the engagement guide portion 106 and engaged with the housing groove 102.

Referring to FIGS. 7 and 8, the engagement guide portion 106 includes an engagement guide path 108 that guides the engagement member 100 led out from the lead-out port 74 to the opening 104 of the housing groove 102, and a deformation generation portion 110 connected to the opening 104 of the housing groove 102 in the engagement guide path 108. The deformation generation portion 110 comes into contact with the engagement member 100 that advances in the Y(+) direction toward the opening 104 in the engagement guide path 108, and guides the engagement member 100 in the X(+) direction while guiding the engagement member 100 in the Y(+) direction.

Accordingly, the distal end side of the wire 60 is elastically deformed in a direction (X(+) direction) to move gradually away from the opening 104 as the engagement member 100 approaches the opening 104 along the engagement guide path 108. When the engagement member 100 has passed through the deformation generation portion 110, the engagement member 100 advancing in the engagement guide path 108 moves in the X(−) direction by the resilient force of the wire 60, and is engaged with the housing groove 102 from the opening 104.

The engagement guide path 108 is formed by cutting a portion of a peripheral surface 28A of the distal end member 28 into a recessed shape, and is a surface that extends from the lead-out port 74 in the Y(+) direction and that is gradually inclined in the X(+) direction. The deformation generation portion 110 is formed on the distal end side of the engagement guide path 108.

Moreover, a groove 112 is formed in the engagement guide portion 106. When the engagement member 100 is engaged with the housing groove 102, the groove 112 allows the distal end side of the wire 60 to fall thereinto and to retract therein. Furthermore, a groove 114 is also formed at the proximal end side of the housing groove 102 of the erecting base 30. When the engagement member 100 is engaged with the housing groove 102, the groove 114 allows the distal end side of the wire 60 to fall thereinto and to retract therein. The width dimension of the groove 112 in a direction orthogonal to the paper face of FIG. 8 is larger than the diameter of the wire 60, and is smaller than the diameter of the engagement member 100 so that the engagement member 100 which passes through the deformation generation portion 110 does not fall into the groove 112. The width dimension of the groove 114 in the direction orthogonal to the paper face of FIG. 8 is larger than the diameter of the wire 60, and is smaller than the diameter of the engagement member 100 so that the engagement member 100 engaged with the housing groove 102 does not come out in the Y(−) direction.

The engagement guide portion 106 has a suitable form for a case where the engagement member 100 is engaged with the housing groove 102 in a state in which the erecting base 30 is located at the erecting position. That is, referring to FIG. 7, the housing groove 102 is arranged at a position facing the lead-out port 74 in the state in which the erecting base 30 is located at the erecting position. Thus, by advancing the engagement member 100 straight from the lead-out port 74, the engagement member 100 can be engaged with the housing groove 102 of the erecting base 30 located at the erecting position, via the engagement guide portion 106.

Next, a detachment structure for detaching the engagement member 100 of the wire 60 engaged with the housing groove 102 of the erecting base 30 from the housing groove 102 is described.

The distal end member 28 includes a detachment guide surface 116. The detachment guide surface 116 is included in an upper surface of the partition wall 80 (see FIG. 2). The detachment guide surface 116 is a guide surface that extends in the X(+) direction and that is inclined in the Z(−) direction (see FIGS. 2 and 3). The detachment guide surface 116 also functions as a surface that guides the wire 60 in a direction in which the engagement member 100 is detached from the inside of the housing groove 102 to the outside of the opening 104 when the wire 60 is operated to be further pushed in a state in which the engagement member 100 is engaged with the housing groove 102 and the erecting base 30 is located at the lying position.

With the thus configured detachment structure, an attachment member (described later) provided at the proximal end of the wire 60 is detached from an engagement hole (described later) of the movable member 96, and then the wire 60 is operated to be pushed from the lead-in port 94 of the extension part 36 to cause the erecting base 30 to be located at the lying position in FIG. 2 from the erecting position in FIG. 3. Then, by further operating the wire 60 to be pushed, the wire 60 is guided in the X(+) direction in which the engagement member 100 is detached from the inside of the housing groove 102 to the outside of the opening 104 by using the detachment guide surface 116 of the distal end member 28. Accordingly, the engagement member 100 is easily detached to the outside of the opening 104 from the inside of the housing groove 102 by the resilient force of the wire 60.

Figure 9:
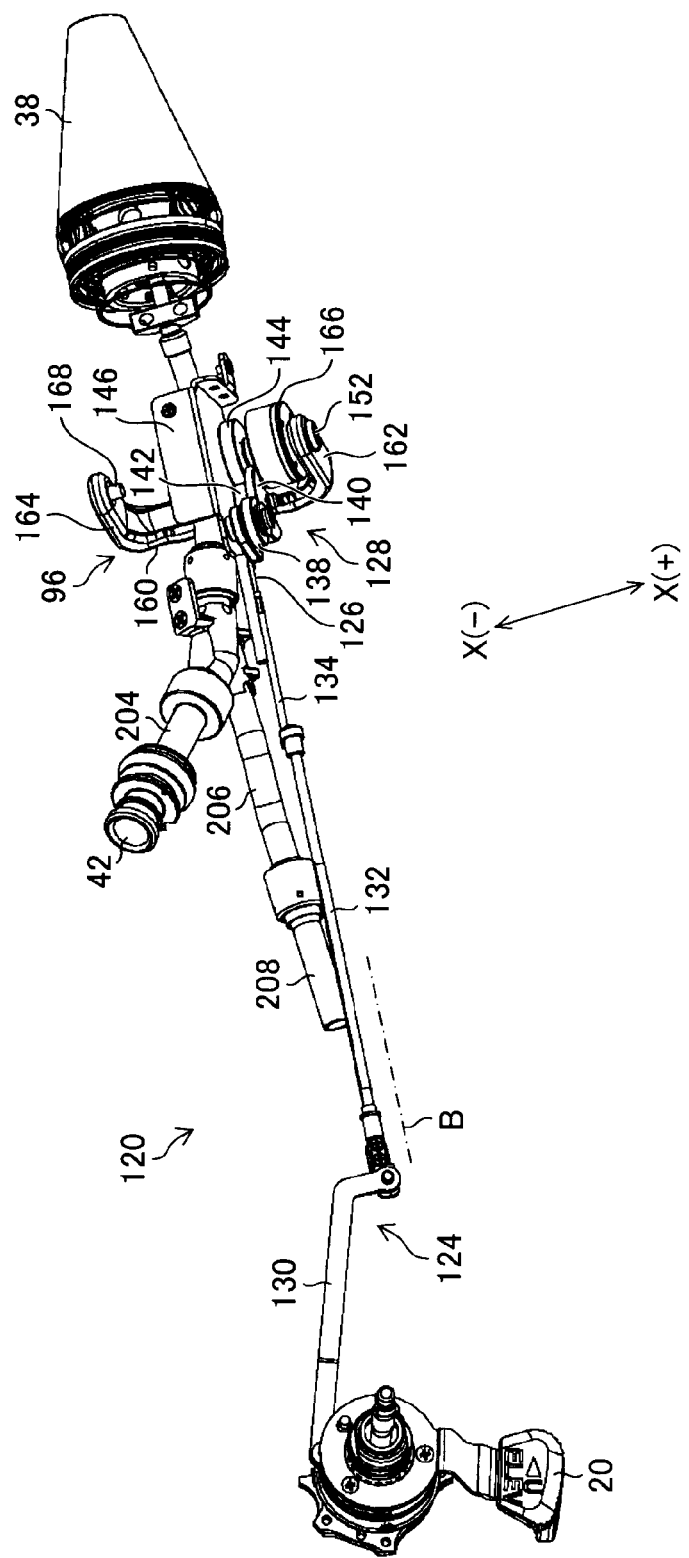
FIG. 9 is a configuration diagram illustrating the entire configuration of an erecting operation mechanism.
Figure 10:
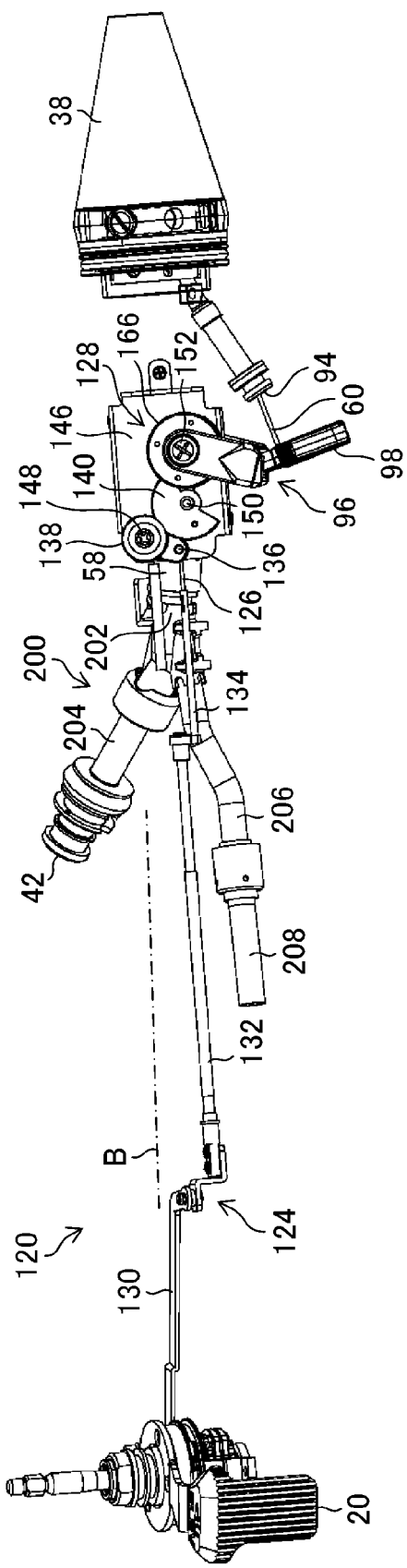
FIG. 10 is a side view of the erecting operation mechanism in FIG. 9.

Next, the erecting operation mechanism 120 illustrated in FIGS. 9 and 10 is described.

FIG. 9 is a configuration diagram illustrating the entire configuration of the erecting operation mechanism 120. FIG. 10 is a side view of the erecting operation mechanism 120 in FIG. 9. FIGS. 9 and 10 omit illustration of an exterior case (not illustrated) of the operation section 22, and illustrate the inside of the operation section 22.

As illustrated in FIGS. 9 and 10, the erecting operation mechanism 120 is provided in the operation section 22.

The erecting operation mechanism 120 is also a power transmission mechanism that couples the erecting operation lever 20 and the movable member 96 to each other and that transmits a rotational movement of the erecting operation lever 20 to the movable member 96.

The erecting operation mechanism 120 includes a first conversion mechanism 124 that converts a rotational motion of the erecting operation lever 20 into a linear motion, a wire 126 that is linearly moved by the first conversion mechanism 124, and a second conversion mechanism 128 that converts the linear motion of the wire 126 into a rotational motion to rotate the movable member 96. The wire 126 is an example of a drive member according to the present invention.

The first conversion mechanism 124 includes a crank member 130 whose proximal end is coupled to the erecting operation lever 20, a first slider 132 whose proximal end is coupled to the distal end of the crank member 130, and a second slider 134 whose proximal end is coupled to the distal end of the first slider 132.

The proximal end of the wire 126 is connected to the distal end of the second slider 134. The distal end of the wire 126 is connected to the second conversion mechanism 128 including a speed reduction mechanism.

With the thus configured first conversion mechanism 124, when the erecting operation lever 20 is rotationally operated, the crank member 130, the first slider 132, and the second slider 134 linearly move along the cylinder axis B in association with the rotational operation. Accordingly, the wire 126 linearly moves along the cylinder axis B, and the linear motion is transmitted to the second conversion mechanism 128.

The second conversion mechanism 128 includes a lever 136, a first gear 138, a second gear 140, a third gear 142, and a fourth gear 144. The first gear 138, the second gear 140, the third gear 142, and the fourth gear 144 configure the speed reduction mechanism.

The lever 136 is rotatably supported by a bracket 146 via a shaft 148. The distal end of the wire 126 is coupled to the lever 136. Thus, the lever 136 is rotated around the shaft 148 by the linear motion of the wire 126.

The first gear 138 is provided integrally with the lever 136, and is rotated around the shaft 148. The second gear 140 is meshed with the first gear 138, and is rotatably supported by the bracket 146 via a shaft 150. The third gear 142 is provided integrally with the second gear 140, and is provided coaxially with the second gear 140. The fourth gear 144 is provided coaxially with a drive shaft 152 of the movable member 96, and is rotatably supported together with the movable member 96 by the bracket 146 via the drive shaft 152. The fourth gear 144 is meshed with the third gear 142.

With the thus configured second conversion mechanism 128, when the linear motion of the wire 126 is transmitted to the lever 136, the first gear 138 is rotationally operated together with the lever 136, the rotational movement of the first gear 138 is transmitted to the fourth gear 144 via the second gear 140 and the third gear 142, and hence the fourth gear 144 is rotated. Accordingly, the movable member 96 integrated with the fourth gear 144 is rotated around the drive shaft 152.

Thus, with the thus configured erecting operation mechanism 120, the rotational operation of the erecting operation lever 20 can be transmitted to the movable member 96 via the first conversion mechanism 124, the wire 126, and the second conversion mechanism 128. Accordingly, the movable member 96 is rotated around the drive shaft 152.

With the erecting operation mechanism 120, the speed of the rotational movement of the erecting operation lever 20 is reduced by the second conversion mechanism 128 including the speed reduction mechanism, and then the rotational movement is transmitted to the movable member 96. That is, the rotation angle of leg portions 162 and 164 of the movable member 96 becomes smaller than the rotation angle of the lever 136 that moves by the operation of the erecting operation lever 20. Accordingly, the force required for operating the erecting operation lever 20 can be further decreased, and the erecting/lying posture of the erecting base 30 can be easily controlled by the erecting operation lever 20.

In the embodiment, the wire 126 is an example of a drive member of the erecting operation mechanism 120 as illustrated in FIGS. 9 and 10. Since the wire 126 is used as the drive member, the following advantages are attained. That is, when the linear motion of the second slider 134 is converted into the rotational motion of the lever 136, the wire 126 has a motion in a curve form (loose), hence a link mechanism is not required to be disposed, and limitation on the space is reduced. When the second slider 134 and the lever 136 are coupled to each other by a link mechanism, a place to which the force escapes is decreased in the erecting operation mechanism 120. In such a case, by using the wire 126, the wire 126 is loosened, hence the force can escape, and the load to be applied to the erecting operation mechanism 120 can be decreased. Thus, even when a certain external force is applied to the movable member 96 exposed to the outside of the operation section 22, the wire 126 is loosened and hence the force can escape, thereby decreasing the load to be applied to the erecting operation mechanism 120.

Figure 18:
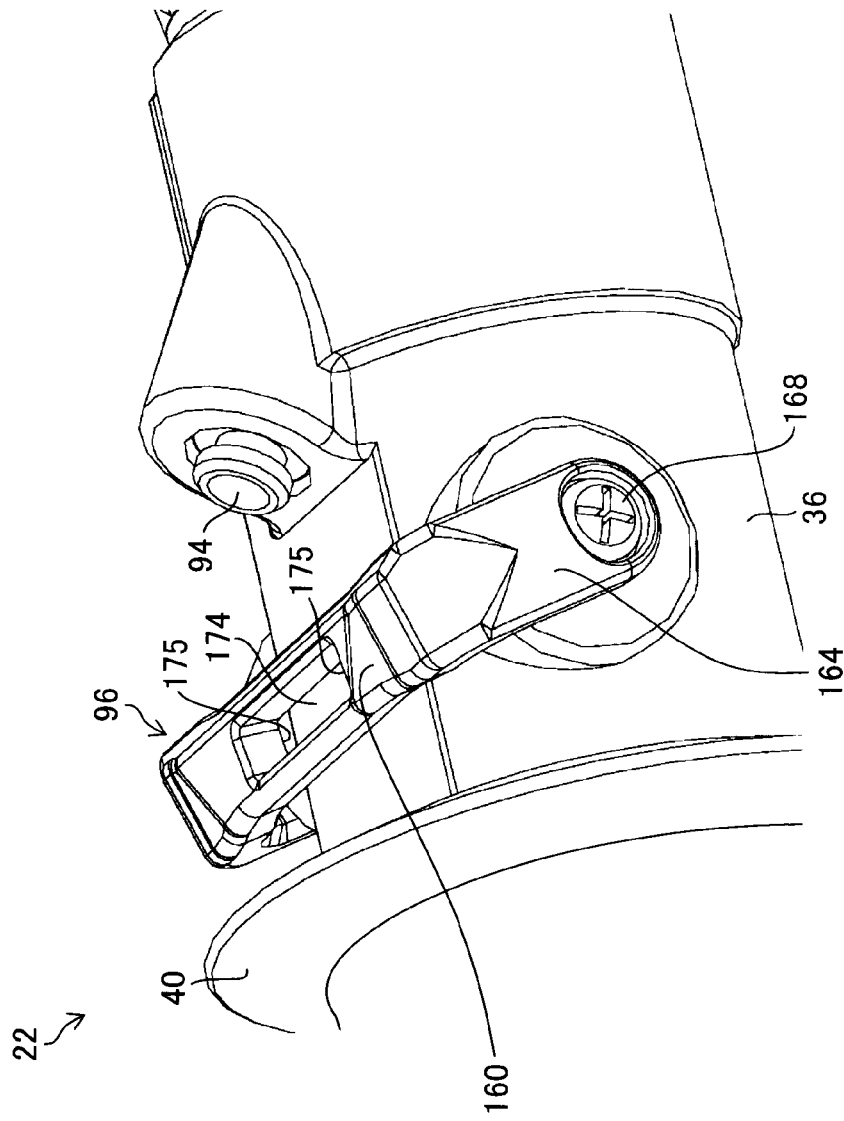
FIG. 18 is a perspective view of an extension part illustrating a lead-in port and a movable member.
Figure 19:
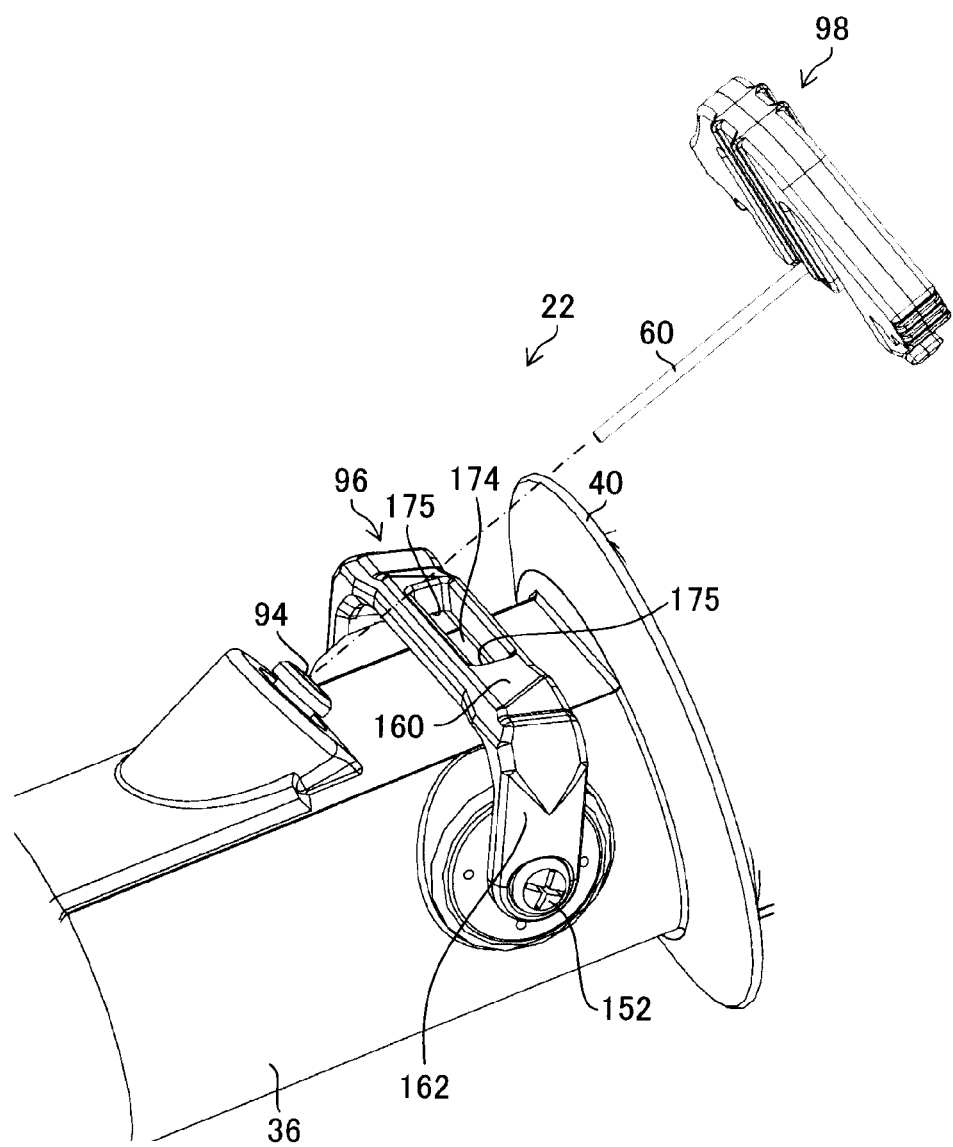
FIG. 19 is an explanatory diagram when a wire is inserted from the lead-in port while an engagement member is at the head.

The shape of the movable member 96 is described here. As illustrated in FIGS. 18 and 19 (described later), the movable member 96 includes a flat-plate-shaped beam portion 160, and the leg portions 162 and 164 provided on both ends of the beam portion 160. The movable member 96 is formed in a U-like shape as a whole. Referring to FIGS. 9 and 10, the drive shaft 152 provided on the leg portion 162 side is rotatably supported by the exterior case (not illustrated) of the operation section 22 via an O-ring 166, and a driven shaft 168 provided on the leg portion 164 side is rotatably supported by the exterior case (not illustrated) via an O-ring (not illustrated). With the O-ring 166 and the other O-ring, the operation section 22 is held watertight.

The rotation axes of the drive shaft 152 and the driven shaft 168 of the movable member 96 are set in a direction (X(+)-X(−) direction) perpendicular to the axial direction of the wire 60. That is, since the movable member 96 is rotatably provided while the direction perpendicular to the axial direction of the wire 60 serves as the rotation axis, the wire 60 can be smoothly pushed/pulled.

Next, a coupling structure 170 according to a first embodiment that couples the proximal end of the wire 60 to the movable member 96 is described with reference to FIGS. 11 to 18.

Figure 11:
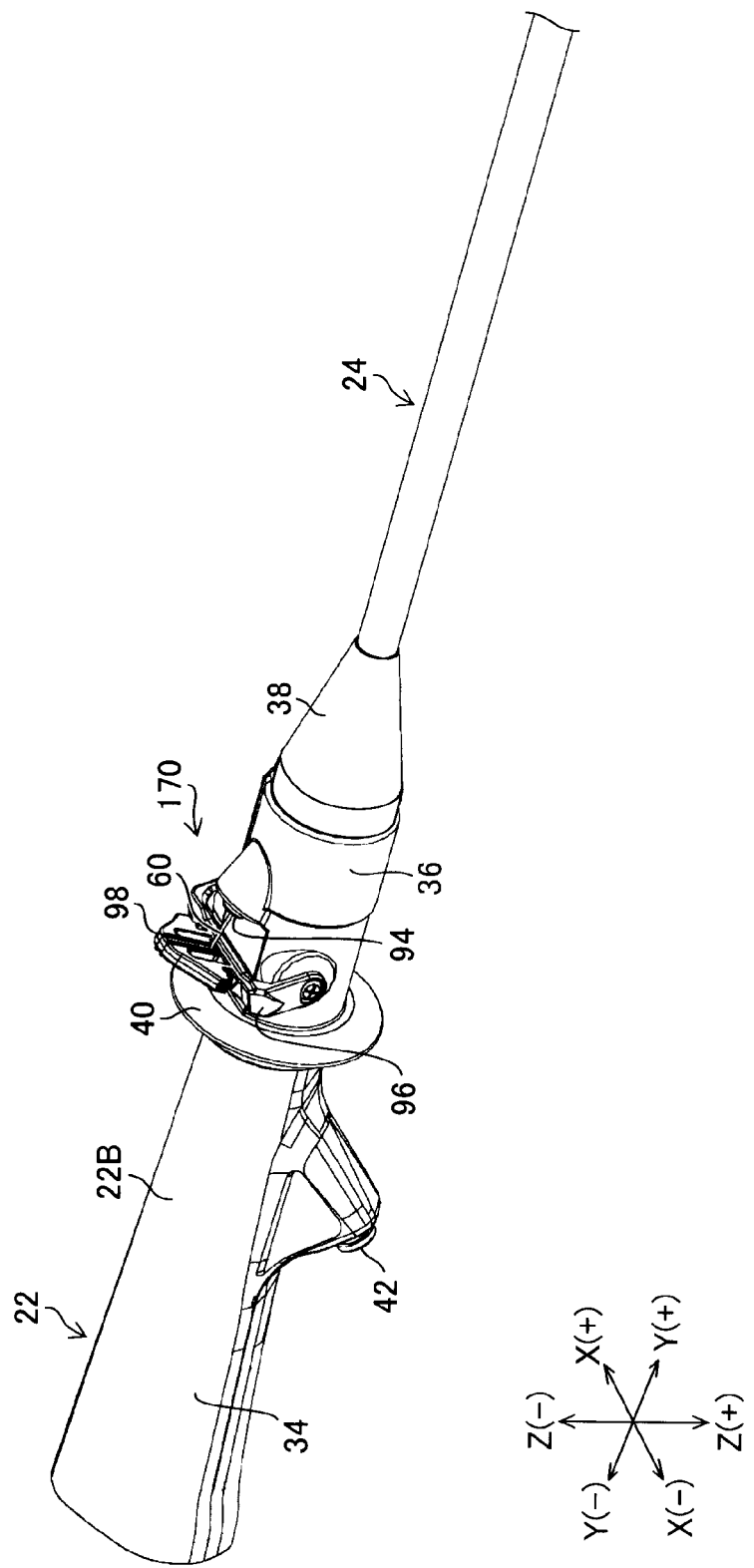
FIG. 11 is a perspective view of a coupling structure according to a first embodiment.
Figure 12:
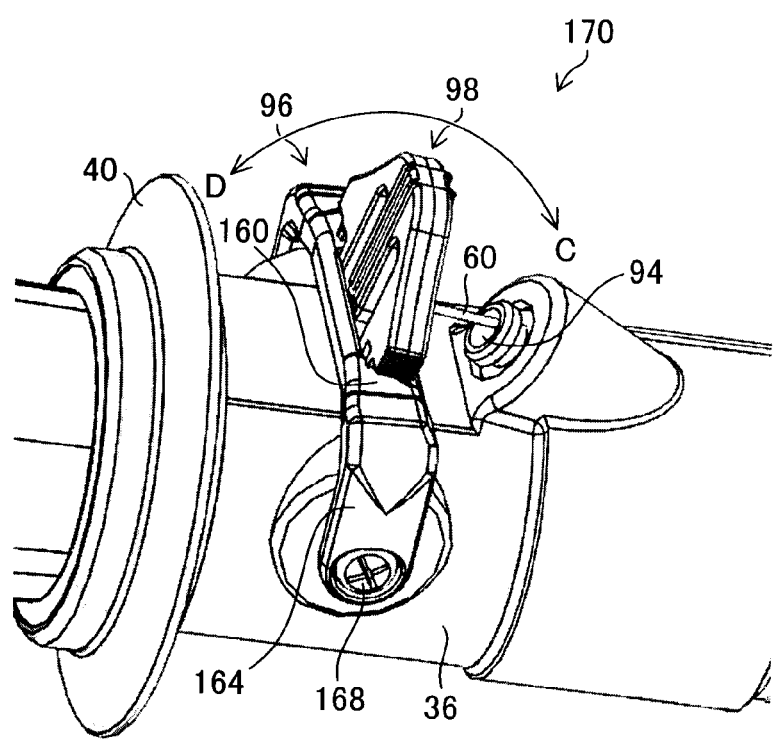
FIG. 12 is a perspective view when the coupling structure illustrated in FIG. 11 is viewed from the left.

FIG. 11 is a perspective view when the coupling structure 170 is viewed from the other side surface 22B of the operation section 22. FIG. 12 is a perspective view when the coupling structure 170 illustrated in FIG. 11 is viewed from the left.

Figure 13:
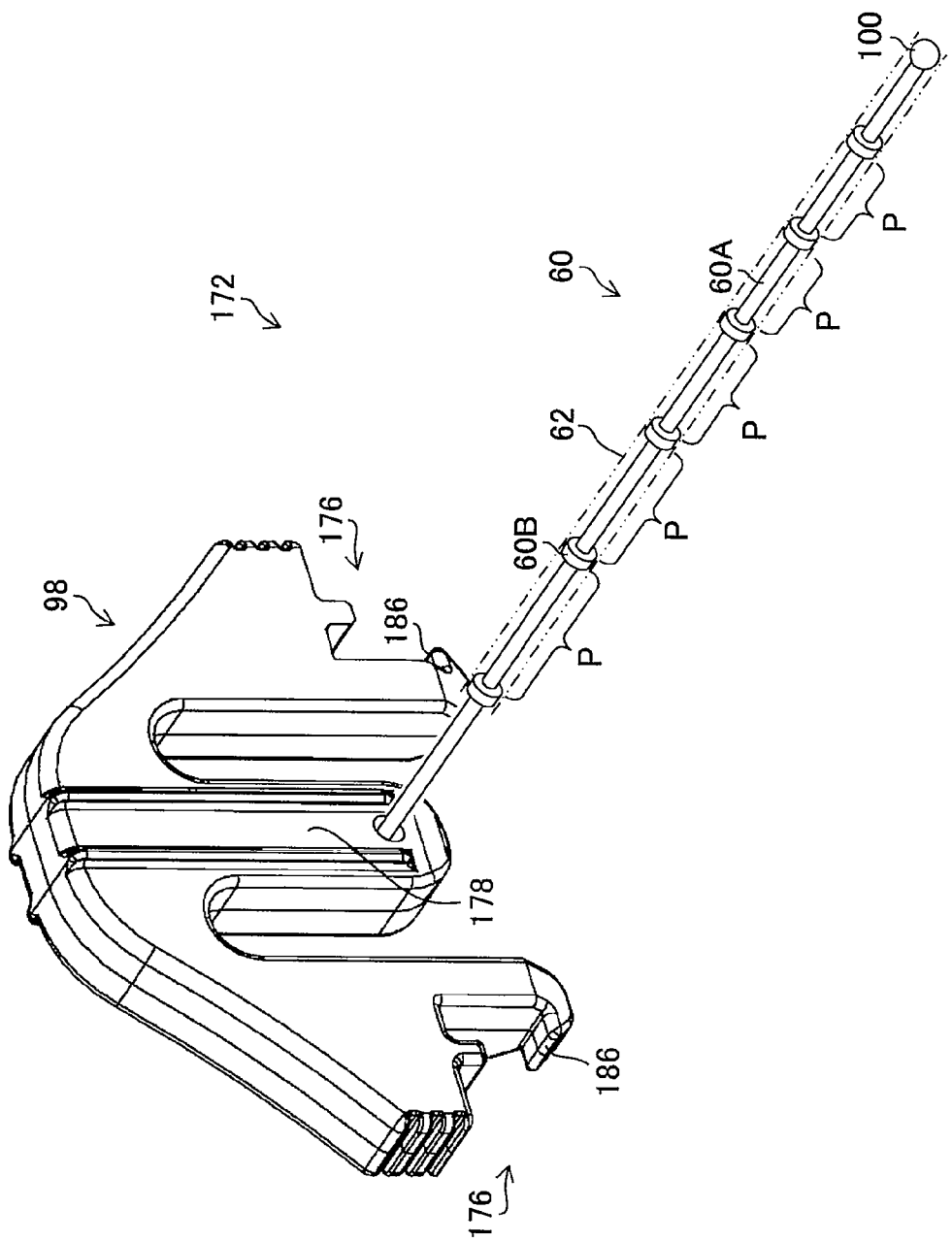
FIG. 13 is a perspective view of a wire assembly.
Figure 15:
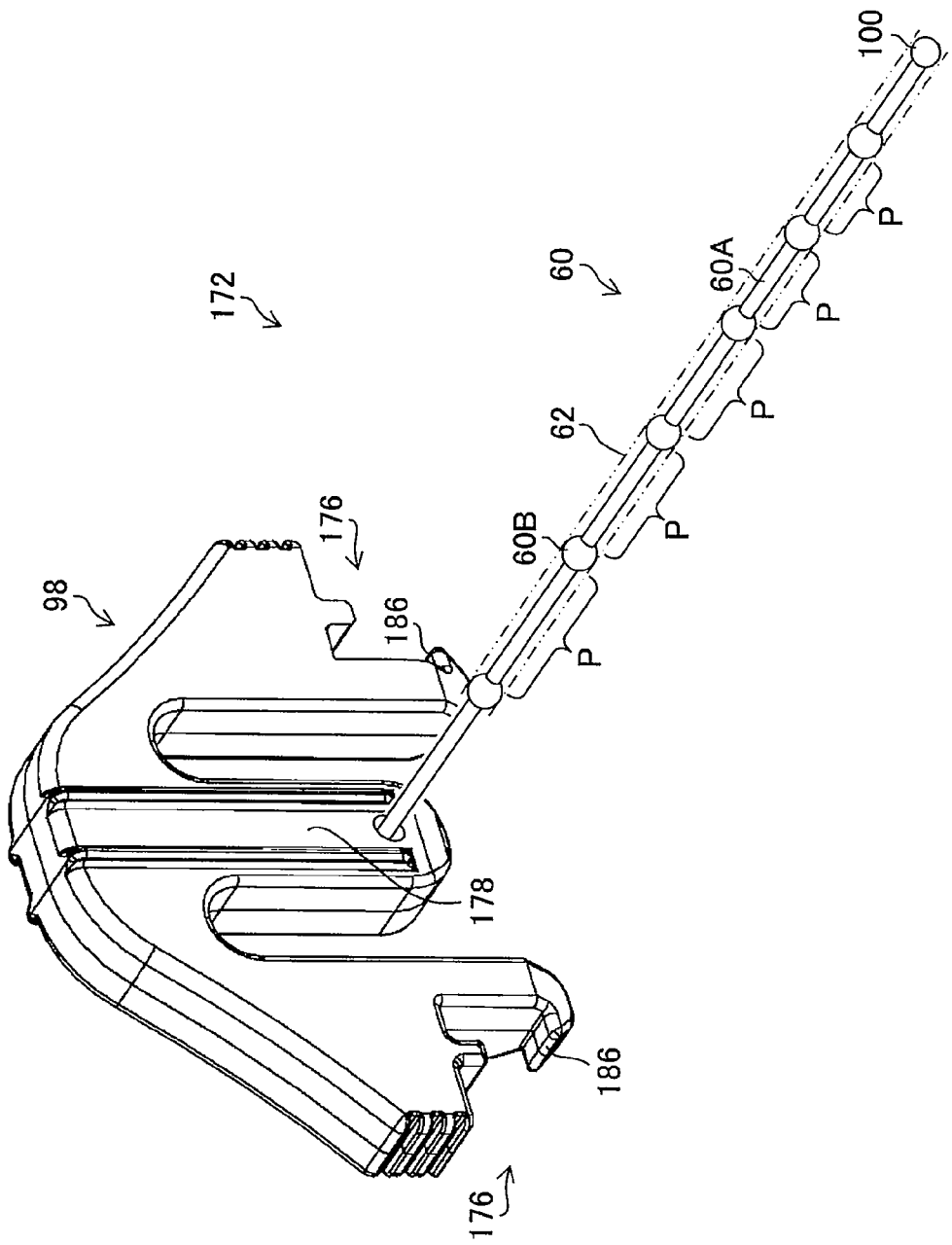
FIG. 15 is a perspective view of a wire assembly.
Figure 17:
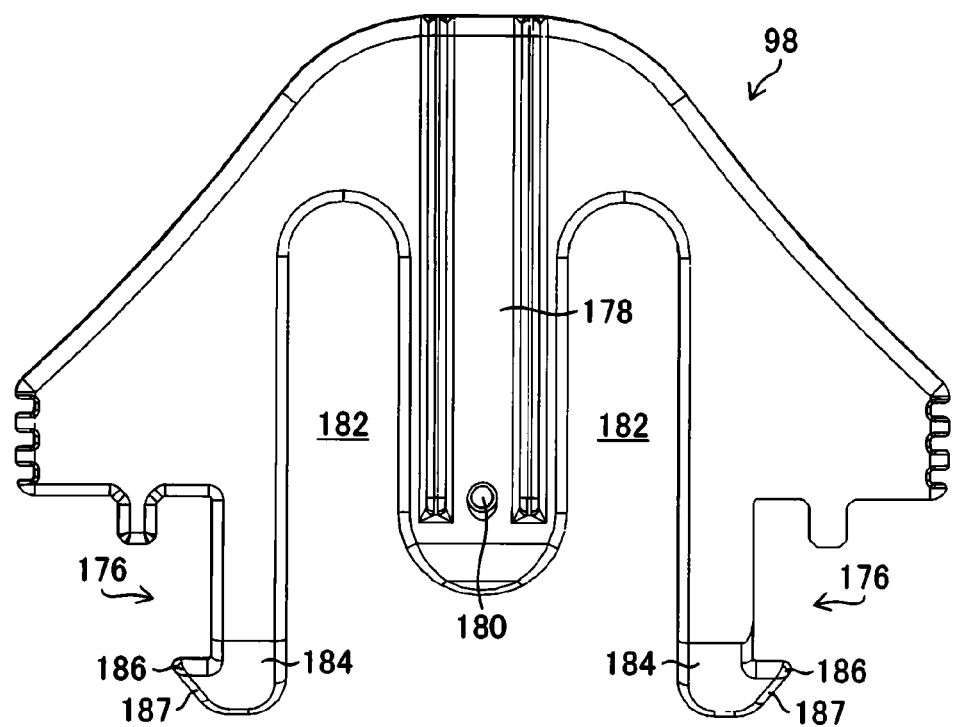
FIG. 17 is a front view of an attachment member.

FIG. 13 is a perspective view of a wire assembly 172 including the wire 60 and the attachment member 98 provided at the proximal end of the wire 60. FIG. 17 is a front view of the attachment member 98. FIG. 15 is a perspective view of the extension part 36 illustrating the lead-in port 94 and the movable member 96.

FIGS. 11 to 18 are explanatory diagrams for illustrating the coupling structure 170. FIGS. 11 and 12 illustrate a state in which the proximal end of the wire 60 and the movable member 96 are coupled by the coupling structure 170. FIGS. 13 to 18 illustrate the attachment member 98 and the movable member 96 that configure the coupling structure 170.

As illustrated in FIG. 13, in the embodiment, the wire 60 includes a flexible long wire body 60A, and a gap filling member 60B arranged at at least a portion in the axial direction of the wire body 60A.

As illustrated in FIGS. 2 and 3, in the embodiment, the distal end of the wire 60 is provided with an engagement member 100. To insert the engagement member 100 through the wire channel 62, a wire channel 62 having an inside diameter that is larger than the diameter of the engagement member 100 is required. Hence it is difficult to conform the inside diameter of the wire channel 62 to the diameter of the wire body 60A, and the clearance is increased. Thus, the wire 60 may meander in the wire channel 62 in a direction orthogonal to the axial direction of the wire 60. When the wire 60 meanders, a trouble occurs in an operation of the erecting base 30, and it is difficult to move the erecting base 30 to a requested lying position. The erecting base 30 at the lying position may exceed a surface of the partition wall 78 with the illumination window 90 and the observation window 92 formed, and insertion performance may not be sufficient when the distal end part 26 is inserted into a body.

The gap filling member 60B is formed to have a diameter that is larger than the outside diameter of the wire body 60A and that is smaller than the inside diameter of the wire channel 62. Thus, the wire 60 can be inserted through the wire channel 62.

When the engagement member 100 is provided at the distal end of the wire 60, the gap filling member 60B preferably has an outside diameter that is equal to or larger than the diameter of the engagement member 100. The gap filling member 60B represents a member for decreasing the clearance between the wire body 60A and the inner wall of the wire channel 62. In the embodiment, a plurality of gap filling members 60B are provided.

The effect of the gap filling member 60B is described below. When the wire body 60A has the engagement member 100 at the distal end thereof, to insert the wire 60 through the wire channel 62, the inside diameter of the wire channel 62 is required to be larger than the outside diameter of the engagement member 100. The clearance between the wire body 60A and the inner wall of the wire channel 62 is increased. If the clearance is increased, when the wire 60 is inserted through the wire channel 62, or when the wire 60 is operated to be pushed/pulled, the wire 60 may meander in the wire channel 62 in a direction orthogonal to the axial direction of the wire channel 62. If the wire 60 meanders, it is difficult to insert the wire 60, it is difficult to couple the erecting base 30 and the engagement member 100 to each other, and it is difficult to correctly operate the erecting base 30 (not illustrated). Since the gap filling member 60B is provided at the wire body 60A, the clearance between the inner wall of the wire channel 62 and the gap filling member 60B is decreased. That is, the clearance between the wire 60 and the inner wall of the wire channel 62 can be decreased. Since the clearance is decreased, the gap filling member 60B can come into contact with the inner surface of the wire channel 62, and the wire 60 can be prevented from meandering. That is, when the wire 60 is pushed, meandering of the wire 60 can be restricted in the wire channel 62, and the erecting base 30 can be moved to the requested lying position. In other words, the erecting base 30 at the lying position can be moved to a position at which the erecting base 30 does not exceed a surface (see FIG. 2) of the partition wall 78 with the illumination window 90 and the observation window 92 formed. Thus, when the distal end part 26 is inserted into the body, insertion performance at high level can be ensured.

The clearance between the inner wall of the wire channel 62 and the gap filling member 60B is preferably 0.05 mm or smaller.

Next, the preferable shape and arrangement of the gap filling member 60B are described below. As illustrated in FIG. 13, a plurality of gap filling members 60B are arranged at mutually different positions in the axial direction of the wire body 60A. The gap filling members 60B are configured of, for example, a columnar expansion portion. When each of the gap filling members 60B has, for example, a columnar shape with a length of 1 mm, the plurality of gap filling members 60B are arranged at a pitch P of 30 mm.

As described above, since the clearance between the inner wall of the wire channel 62 and the gap filling members 60B is small, the gap filling members 60B come into contact with the inner surface of the wire channel 62. The contact causes insertion resistance when the wire 60 is inserted through the wire channel 62, or causes pull resistance when the wire 60 is operated. The length and pitch P of the gap filling members 60B are determined with regard to the insertion resistance and pull resistance of the wire 60 as well as prevention of meandering of the wire 60. Since the length of each of the gap filling members 60B is 1 mm, the contact area between the gap filling members 60B and the inner surface of the wire channel 62 can be decreased, thereby decreasing the insertion resistance and pull resistance.

It is to be noted that the pitch P between the gap filling member 60B arranged on the proximal end side of the wire body 60A and the adjacent gap filling member 60B is preferably larger than the pitch P between the gap filling members 60B arranged at other positions. The pitch P is preferably changed in accordance with the relative positions of the wire body 60A and the wire channel 62.

As illustrated in FIG. 11, the wire 60 is inserted through the lead-in port 94 in a direction oblique to the axial direction of the extension part 36 and the break prevention pipe 38. The wire 60 is bent by the wire channel 62 located at the extension part 36 and the break prevention pipe 38, and is guided to the insertion section 24. At a position at which the wire 60 is bent, the contact force between the gap filling members 60B and the inner wall of the wire channel 62 may be increased, and the friction may be increased.

Thus, by increasing the pitch P, it is preferable to decrease the gap filling members 60B per unit length, and to decrease the contact portions between the gap filling members 60B and the inner wall of the wire channel 62 at the position at which the wire 60 is bent. The friction at the position at which the wire 60 is bent can be decreased.

To decrease the friction, the shape of each of the gap filling members 60B may be changed from the columnar shape into a spherical shape. The spherical gap filling member 60B decreases the contact area with the inner wall of the wire channel 62 and decreases the friction. The shape of the gap filling member 60B is preferably changed in accordance with the position of the wire body 60A.

Similarly to the proximal end portion of the wire 60, the contact force between the wire channel 62 and the gap filling members 60B may be increased at the bending part 52 (not illustrated), and the friction may be increased. At the position corresponding to the bending part 52, it is preferable to increase the size of the pitch P between the gap filling members 60B or to make the shape of each of the gap filling members 60B be spherical.

Figure 14:
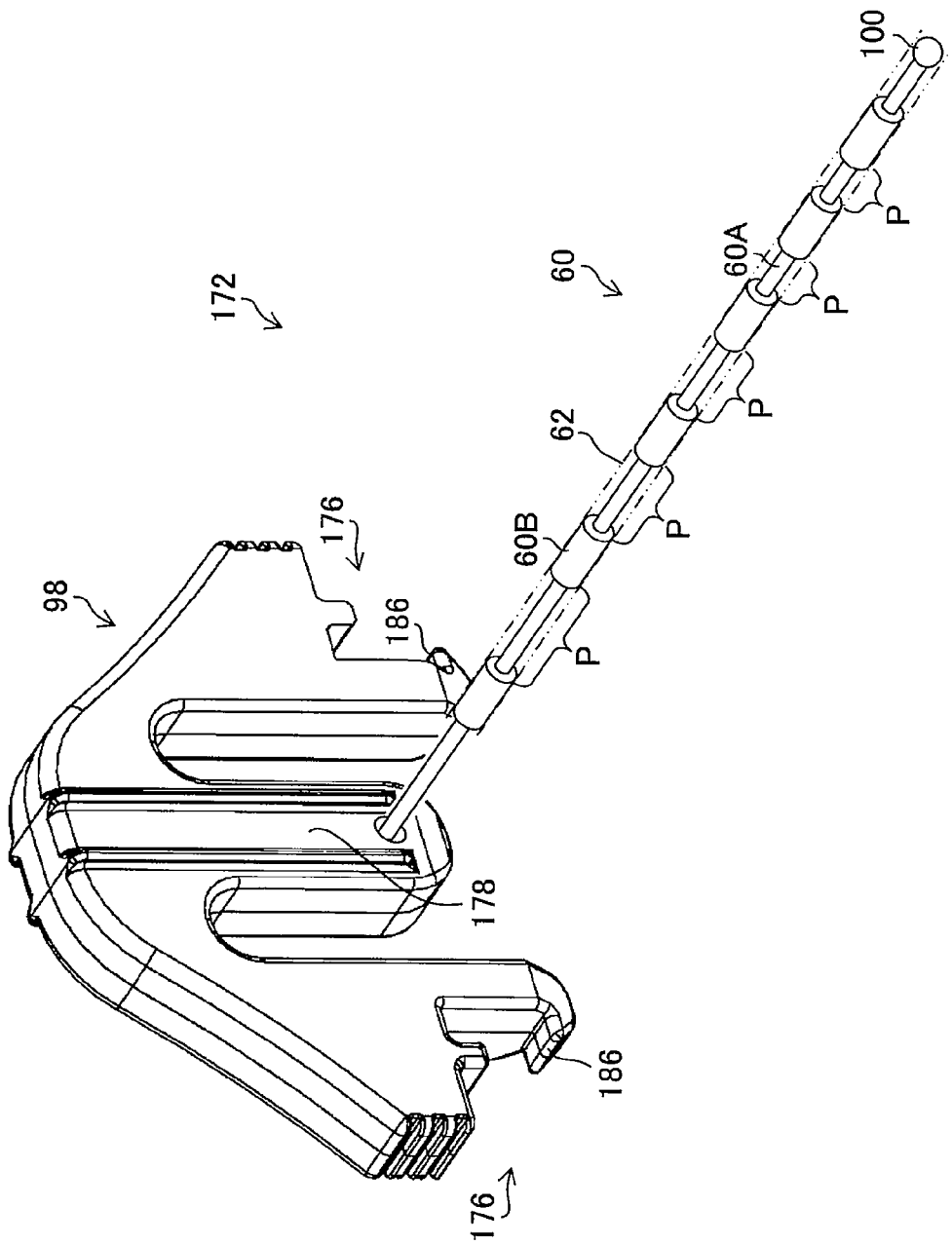
FIG. 14 is a perspective view of a wire assembly.

FIG. 14 illustrates the shape of a modification of the gap filling members 60B in FIG. 13. The gap filling members 60B illustrated in FIG. 14 are each configured of a columnar expansion portion. The length of the gap filling member 60B in FIG. 14 is larger than that of the gap filling member 60B in FIG. 13. For example, when the gap filling member 60B has a length of 4 mm, the pitch P is 50 mm. When the length of the gap filling member 60B is large, the effect of the prevention of meandering of the wire 60 is increased. The pitches P of the gap filling members 60B may be equivalent distances or may be changed in accordance with the relative positions of the wire body 60A and the wire channel 62. All the plurality of gap filling members 60B may have columnar shapes, or some of the gap filling members 60B may have shapes other than the columnar shapes.

FIG. 15 illustrates gap filling members 60B each having a shape different from the shapes in FIGS. 13 and 14. The gap filling members 60B illustrated in FIG. 15 are each configured of a spherical expansion portion. The pitches P of the gap filling members 60B may be equivalent distances or may be changed in accordance with the position of the wire body 60A. All the plurality of gap filling members 60B may have spherical shapes, or some of the gap filling members 60B may have shapes other than the spherical shapes.

Examples of the preferable material configuring the gap filling members 60B illustrated in FIGS. 13 to 15 include a resin material such as polyoxymethylene (POM), or metal.

When the gap filling members 60B are hard and long, the gap filling members 60B may have difficulty in passing through a portion at which the channel is bent from the lead-in port 94. The angle at which the channel is bent from the lead-in port 94 is eased or the material of the gap filling members 60B is changed to a soft member such as rubber, so that the gap filling members 60B can easily pass through the bent portion. The gap filling members 60B may be integrally formed with the wire body 60A or may be formed separately from the wire body 60A.

Figure 16:
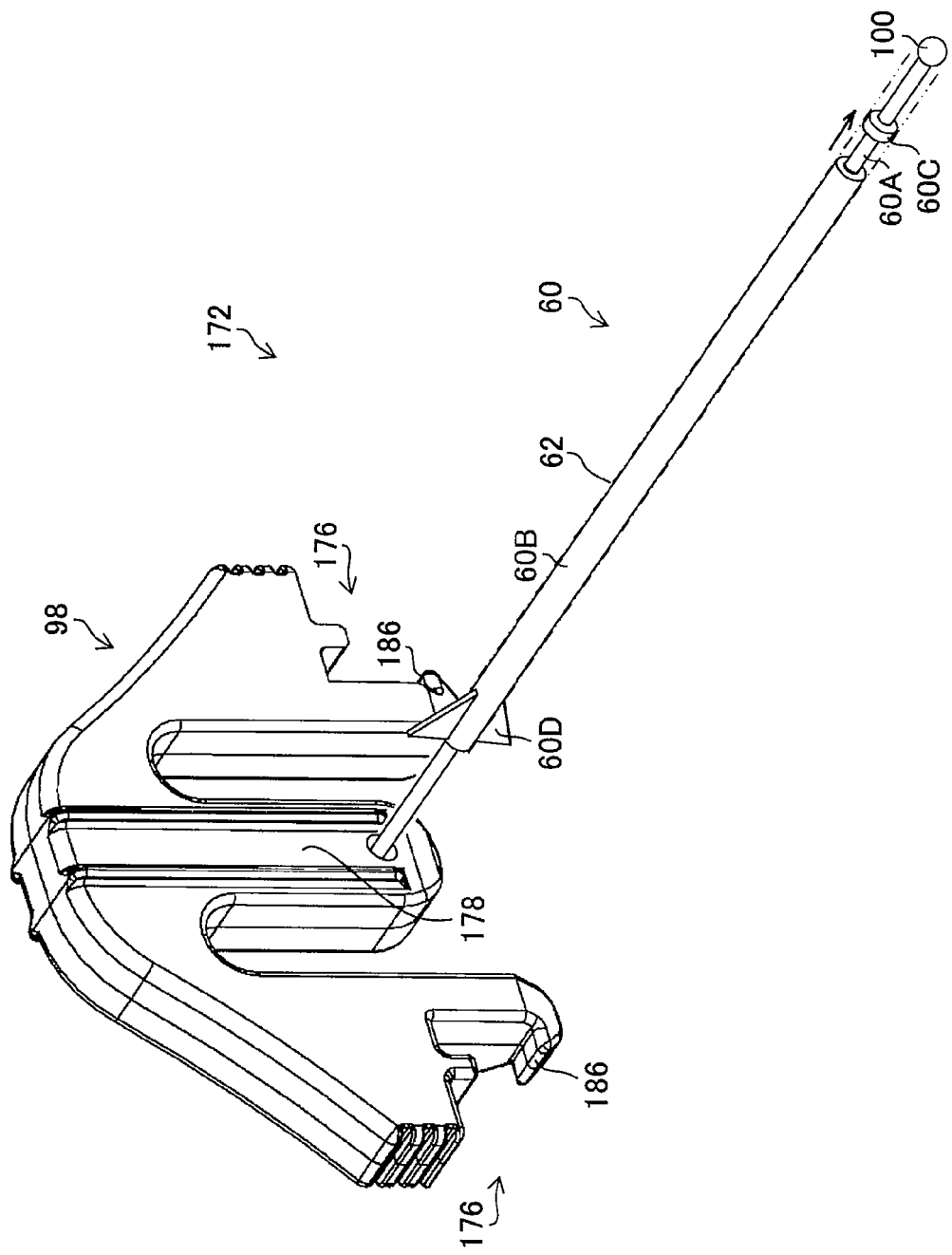
FIG. 16 is a perspective view of a wire assembly.

FIG. 16 illustrates gap filling members 60B each having a shape different from the shapes in FIGS. 13 to 15. The gap filling members 60B illustrated in FIG. 16 are each configured of a long outer layer member disposed on the outer periphery side of the wire body 60A and extending in the axial direction of the wire body 60A.

The shape and material of the outer layer member are not particularly limited as long as the outer layer member is arranged on the outer periphery side of the wire body 60A, can cover the wire body 60A, and can fill the clearance between the inner wall of the wire channel 62 and the wire body 60A.

As illustrated in FIG. 16, the gap filling member 60B is arranged to cover substantially the entire region of the wire body 60A. For the shape of the gap filling member 60B, for example, any one of a coil spring, a hollow wire, a heat shrinkable tube, and coating may be applied. The coil spring may be dense coiling, rough coiling, or a combination of the dense coiling and the rough coiling. The hollow wire represents a pipe shape having openings at both ends, and includes a tubular structure, a structure formed by braiding a plurality of wires to have a hollow at the center, or the like. The heat shrinkable tube represents a tubular member that has openings at both ends thereof and that shrinks in a direction in which the diameter of the heat shrinkable tube is decreased when being heated. The coating includes, for example, a structure formed on the outer peripheral surface of the wire body 60A through application of coating by dip coating or the like.

One of the coil spring, the hollow wire, the heat shrinkable tube, and the coating applied to FIG. 16 may be applied to the columnar gap filling members 60B illustrated in FIGS. 14 and 15.

The gap filling member 60B configured of the outer layer member can be fixed to the wire body 60A. The wire 60 in which the wire body 60A is fixed to the gap filling member 60B is inserted through the wire channel 62 (not illustrated).

The gap filling member 60B configured of the outer layer member can be configured of a tubular body through which the wire body 60A can be inserted to allow the wire body 60A to freely advance/retract therethrough. The gap filling member 60B can be easily arranged on the outer periphery of the wire body 60A and the position of the gap filling member 60B can be easily determined.

For the gap filling member 60B that can be inserted to allow the wire body 60A to freely advance/retract therethrough, any one of a coil spring, a hollow wire, and a normal tube may be used. For the gap filling member 60B, a tubular body having a configuration in which a slit is formed to extend along the axial direction of the gap filling member 60B and the wire body 60A is arranged in a hollow portion of the gap filling member 60B through the slit may be used.

As illustrated in FIG. 16, when the gap filling member 60B allows the wire body 60A to freely advance/retract therethrough, a first position regulation portion 60C is preferably included at the distal end side. The distal end of the gap filling member 60B comes into contact with the first position regulation portion 60C, and hence the distal end of the gap filling member 60B can be prevented from entering the erecting base housing chamber 82.

As illustrated in FIG. 16, the gap filling member 60B includes a second position regulation portion 60D at the proximal end side. The second position regulation portion 60D comes into contact with the lead-in port 94 (not illustrated) as described later, and hence the distal end of the gap filling member 60B can be prevented from entering the erecting base housing chamber 82.

The length of the gap filling member 60B from the distal end to the engagement member 100 (that is, the length of an exposure region of the wire body 60A) is preferably a length required for the erecting base 30 (not illustrated) to rotate between the erecting position and the lying position. In a state in which the erecting base 30 is at the lying position, the gap filling member 60B is preferably not to be exposed to the inside of the erecting base housing chamber 82 (not illustrated).

In the case where the gap filling member 60B is configured of the tubular body that allows the wire body 60A to freely advance/retract therethrough, the embodiment illustrated in FIG. 16 provides the wire 60 including the first position regulation portion 60C and the second position regulation portion 60D. However, the structure of the wire 60 is not limited to this structure. The wire 60 may include one of the first position regulation portion 60C and the second position regulation portion 60D. Since the wire 60 includes one of the first position regulation portion 60C and the second position regulation portion 60D, the distal end of the gap filling member 60B is prevented from entering the erecting base housing chamber 82.

The gap filling member 60B is inserted into the wire channel 62, and the wire body 60A is inserted through the hollow portion of the gap filling member 60B. Thus, meandering of the wire 60 is prevented.

As illustrated in FIG. 18, the movable member 96 includes an engagement hole 174 with which the attachment member 98 is engaged in an attachable/detachable manner by a one-touch operation. The engagement hole 174 is formed along the longitudinal direction of the beam portion 160 of the movable member 96, and is configured of a through hole extending through the front and back surfaces of the beam portion 160. A pair of engagement portions 176 (see FIG. 17) of the attachment member 98 are engaged with the engagement hole 174 in an attachable/detachable manner by a one-touch operation. That is, the attachment member 98 is engaged with the movable member 96 in an attachable/detachable manner by a one-touch operation. Accordingly, with the coupling structure 170 according to the first embodiment, the proximal end of the wire 60 and the movable member 96 are coupled to each other outside the operation section 22. Alternatively, the engagement hole 174 may be a recessed non-through hole not extending through the front and back surfaces of the beam portion 160.

In this specification, being "engaged in an attachable/detachable manner by a one-touch operation" represents that a movement for attachment of the attachment member 98 to the movable member 96 and a movement for detachment of the attachment member 98 from the movable member 96 can be performed only by the movement of the attachment member 98 relative to the movable member 96 without using another fixing tool (for example, a screw, a bolt, or a nut). This is applied to other embodiments (described later).

The attachment member 98 illustrated in FIG. 17 is a substantially triangular plate-shaped body, and has a hole portion 180 at a core portion 178 of a center portion of the attachment member 98. The proximal end of the wire 60 is coupled to the hole portion 180. The engagement portions 176 of the attachment member 98 are provided on both sides of the core portion 178 with slit-shaped cut portions 182 interposed between the engagement portions 176 and the core portion 178. The engagement portions 176 are provided with a pair of elastic deformation portions 184 that are elastically deformed and engaged with the engagement hole 174. The elastic deformation portions 184 have a pair of claw portions 186 at edge portions 175 (see FIGS. 18 and 19) on both sides in the longitudinal direction of the engagement hole 174. The pair of claw portions 186 are displaced in directions to move toward each other by elastic deformation of the pair of elastic deformation portions 184 when the engagement portions 176 are engaged with or disengaged from the engagement hole 174.

Next, the coupling procedure of the proximal end of the wire 60 and the movable member 96 to each other with the coupling structure 170 according to the first embodiment is described with reference to FIGS. 19 to 21.

Before the proximal end of the wire 60 and the movable member 96 are coupled to each other, the distal end of the wire 60 is coupled to the erecting base 30.

FIG. 19 illustrates a state in which the wire 60 is inserted from the lead-in port 94 while the engagement member 100 (see FIGS. 13 to 16) is at the head. With the insertion operation of the wire 60, the distal end of the wire 60 is coupled to the erecting base 30.

That is, in the state in which the erecting base 30 is located at the erecting position (see FIG. 3), referring to FIG. 19, when the wire 60 is led in from the lead-in port 94 while the engagement member 100 is at the head, the engagement member 100 is inserted through the wire channel 62 (see FIG. 2) and is led out to the outside from the lead-out port 74. The engagement member 100 is guided by the engagement guide portion 106 in FIG. 3 toward the opening 104 of the housing groove 102 of the erecting base 30 through the ongoing lead-in operation of the wire 60, and is engaged with the housing groove 102 from the opening 104. Accordingly, the distal end of the wire 60 is coupled to the erecting base 30.

Figure 20:
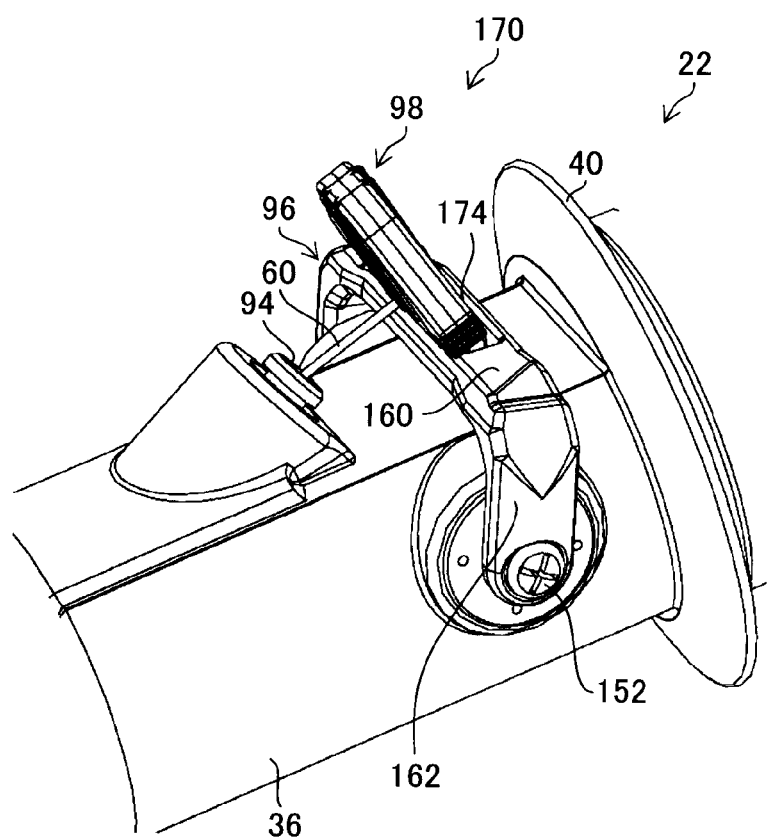
FIG. 20 is an explanatory diagram of the attachment member in a state in which the distal end of the wire is coupled to the erecting base.
Figure 21:
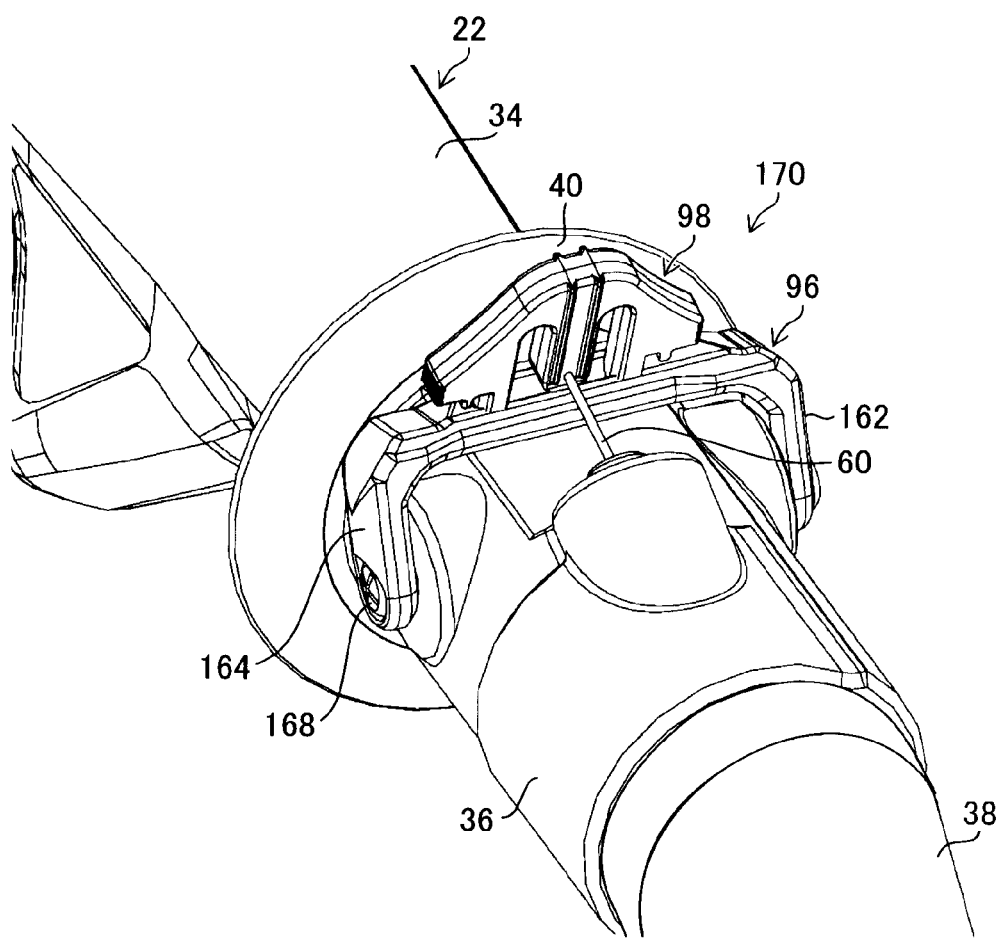
FIG. 21 is an explanatory diagram when the attachment member is coupled to the movable member.

FIG. 20 illustrates the state of the attachment member 98 in a state in which the distal end of the wire 60 is coupled to the erecting base 30. In this state, tapered portions 187 located below the claw portions 186 are brought into contact with edges on both sides of the engagement hole 174 and are pushed into the engagement hole 174. With this movement, the distance between the claw portions 186 is decreased, the claw portions 186 are latched to the edge portions 175 on both sides of the engagement hole 174, and the attachment member 98 is coupled to the movable member 96 referring to the coupling diagram of FIG. 21.

Accordingly, with the coupling structure 170 according to the first embodiment, the movement for attachment of the attachment member 98 to the movable member 96 can be performed only by the movement of the attachment member 98 relative to the movable member 96. That is, with the coupling structure 170 according to the first embodiment, the attachment member 98 can be engaged with the movable member 96 by a one-touch operation.

When the attachment member 98 is mounted at the movable member 96, the pair of engagement portions 176 of the attachment member 98 can be pinched with fingers of a hand to narrow the distance between the claw portions 186 to be smaller than the dimension in the longitudinal direction of the engagement hole 174. That is, the pair of elastic deformation portions 184 are displaced in directions to move toward each other by elastic deformation. After the claw portions 186 are inserted into the engagement hole 174, by relaxing the force of the fingers of the hand to expand the distance between the claw portions 186, the claw portions 186 are latched to the edge portions 175 on both sides of the engagement hole 174. Accordingly, the attachment member 98 is engaged with the movable member 96 by a one-touch operation.

Then, when the erecting operation lever 20 in FIG. 1 is operated, as illustrated in the movement explanatory diagram of the movable member 96 in FIG. 12, the movable member 96 moves in a direction of arrow C or arrow D. Then, in association with the movement of the movable member 96, the wire 60 is operated to be pushed/pulled by the movable member 96 via the attachment member 98. Accordingly, the erecting base 30 is rotated between the erecting position and the lying position.

According to the embodiment, the engagement hole 174 is formed in the movable member 96 and the engagement portions 176 are formed at the attachment member 98.

However, the engagement portions 176 may be formed at the movable member 96 and the engagement hole 174 may be formed in the attachment member 98. That is, the engagement hole 174 may be provided in one of the movable member 96 and the attachment member 98, and the engagement portions 176 that are engaged with the engagement hole 174 in an attachable/detachable manner by a one-touch operation may be provided at the other one. The claw portions 186 may not be provided on the sides in the longitudinal direction of the beam portion 160 of the movable member 96, and may be provided on the sides in the transverse direction of the beam portion 160. The engagement hole 174 may be two engagement holes formed to be spaced apart in the longitudinal direction of the beam portion 160.

The endoscope 10 is used for one of various inspections or one of various treatments. Thereafter, when the endoscope 10 is washed, the following works are performed.

First, the cap 76 illustrated in FIG. 2 is removed from the distal end member 28. Then, the engagement portions 176 of the attachment member 98 are removed from the engagement hole 174 (see FIG. 18) of the movable member 96, and the wire 60 is removed from the movable member 96. Then, the wire 60 is operated to be pushed from the lead-in port 94 of the extension part 36 to cause the erecting base 30 to be located at the lying position in FIG. 2 from the erecting position in FIG. 3. Then, by further operating the wire 60 to be pushed, the engagement member 100 is detached to the outside of the opening 104 from the inside of the housing groove 102. With the works, the distal end of the wire 60 is removed from the erecting base 30. Then, the wire 60 is pulled out from the lead-in port 94, and the wire channel 62 is made empty. Then, the distal end member 28, the erecting base 30, and the wire channel 62 of the wire 60 are washed.

In the work of removing the distal end of the wire 60 from the erecting base 30, in the coupling structure 170 according to the first embodiment, since the attachment member 98 is coupled to the movable member 96 outside the operation section 22, the attachment member 98 can be easily removed from the movable member 96. Specifically, the pair of engagement portions 176 of the attachment member 98 are pinched with fingers of a hand to narrow the distance between the claw portions 186 to be smaller than the dimension in the longitudinal direction of the engagement hole 174. Then, the claw portions 186 are pulled out from the engagement hole 174.

Accordingly, with the coupling structure 170 according to the first embodiment, the movement for detachment of the attachment member 98 from the movable member 96 can be performed only by the movement of the attachment member 98 relative to the movable member 96. That is, with the coupling structure 170 according to the first embodiment, the attachment member 98 can be detached from the movable member 96 by a one-touch operation.

As described above, with the coupling structure 170 according to the first embodiment, after the distal end of the wire 60 is coupled to the erecting base 30, merely by engaging the engagement portions 176 of the attachment member 98 with the engagement hole 174 of the movable member 96 outside the operation section 22, the proximal end of the wire 60 can be coupled to the movable member 96. When the endoscope 10 is washed, to remove the proximal end of the wire 60 from the movable member 96, merely by detaching the attachment member 98 from the engagement hole 174 of the movable member 96 outside the operation section 22, the proximal end of the wire 60 can be removed from the movable member 96.

Thus, with the coupling structure 170 according to the first embodiment, compared with the endoscope of JP1994-315458A (JP-H6-315458A) that performs the attachment/detachment work of the proximal end of the wire to/from the connecting tool in the operation section and the endoscope of EP1759626B in which the distal end of the cable cord is mounted at the collet and the nut in an attachable/detachable manner, the attachment/detachment operation of the proximal end of the wire 60 to/from the movable member 96 can be easily performed.

In the above-described embodiment, the wire 60 is pulled out from the lead-in port 94. However, the wire 60 may be pulled out from the lead-out port 74 of the distal end member 28. In this case, by removing the attachment member 98 from the proximal end of the wire 60 before the wire 60 is pulled out, the wire 60 can be pulled out from the lead-out port 74.

FIG. 22 is a perspective view illustrating a modification of the coupling structure 170 according to the first embodiment illustrated in FIGS. 11 to 21.

A coupling structure 170A according to a modification illustrated in FIG. 22 is described with the same reference signs applied to the same or similar members as or to those of the coupling structure 170 illustrated in FIGS. 11 to 21.

An engagement hole 174A formed in the movable member 96 is a circular through hole. An engagement portion 176A of an attachment member 98A has a tubular portion 177 that is fitted into the engagement hole 174A. An elastic deformation portion of the attachment member 98A is configured of a slotted portion 184A provided at a distal end portion of the tubular portion 177. A claw portion 186A is formed at the outer peripheral surface of the slotted portion 184A.

Figure 23:
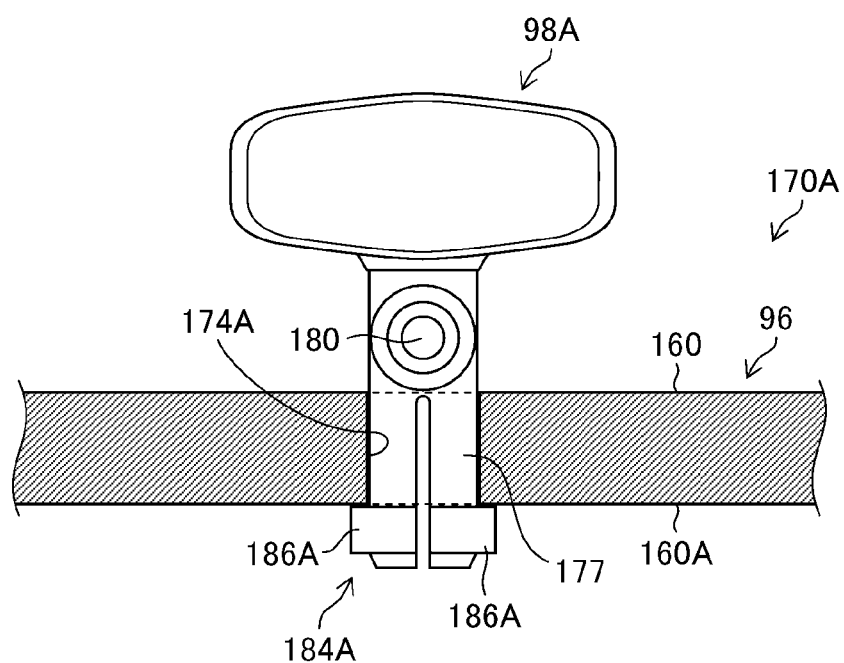
FIG. 23 is a main-part sectional view of the coupling structure illustrated in FIG. 19.

With the thus configured coupling structure 170A, when the slotted portion 184A of the tubular portion 177 is fitted into the engagement hole 174A, the diameter of the slotted portion 184A is decreased by elastic deformation. Accordingly, after the slotted portion 184A is passing through the engagement hole 174A and then the slotted portion 184A has passed through the engagement hole 174A, the diameter of the slotted portion 184A is restored to the original diameter. Thus, referring to the sectional view of the coupling structure 170A illustrated in FIG. 23, the claw portion 186A of the slotted portion 184A is engaged with a back surface 160A of the beam portion 160 of the movable member 96. The attachment member 98A is engaged with the movable member 96 by a one-touch operation.

Even with the coupling structure 170A, the attachment/detachment work of the attachment member 98A to/from the movable member 96 is performed outside the operation section 22 similarly to the coupling structure 170. The attachment work is of merely inserting the engagement portion 176A into the engagement hole 174A. With the attachment work, the proximal end of the wire 60 can be easily coupled to the movable member 96 via the attachment member 98A.

When the attachment member 98A is removed from the movable member 96, the slotted portion 184A is pinched with fingers to decrease the diameter of the slotted portion 184A. Then, the slotted portion 184A is pulled out from the engagement hole 174A.

Accordingly, even with the coupling structure 170A according to the modification, the movement for attachment of the attachment member 98A to the movable member 96 and the movement for detachment of the attachment member 98A from the movable member 96 can be performed only by the movement of the attachment member 98A relative to the movable member 96 similarly to the coupling structure 170. That is, with the coupling structure 170A, the attachment member 98A is engaged with the movable member 96 in an attachable/detachable manner by a one-touch operation.

Figure 24:
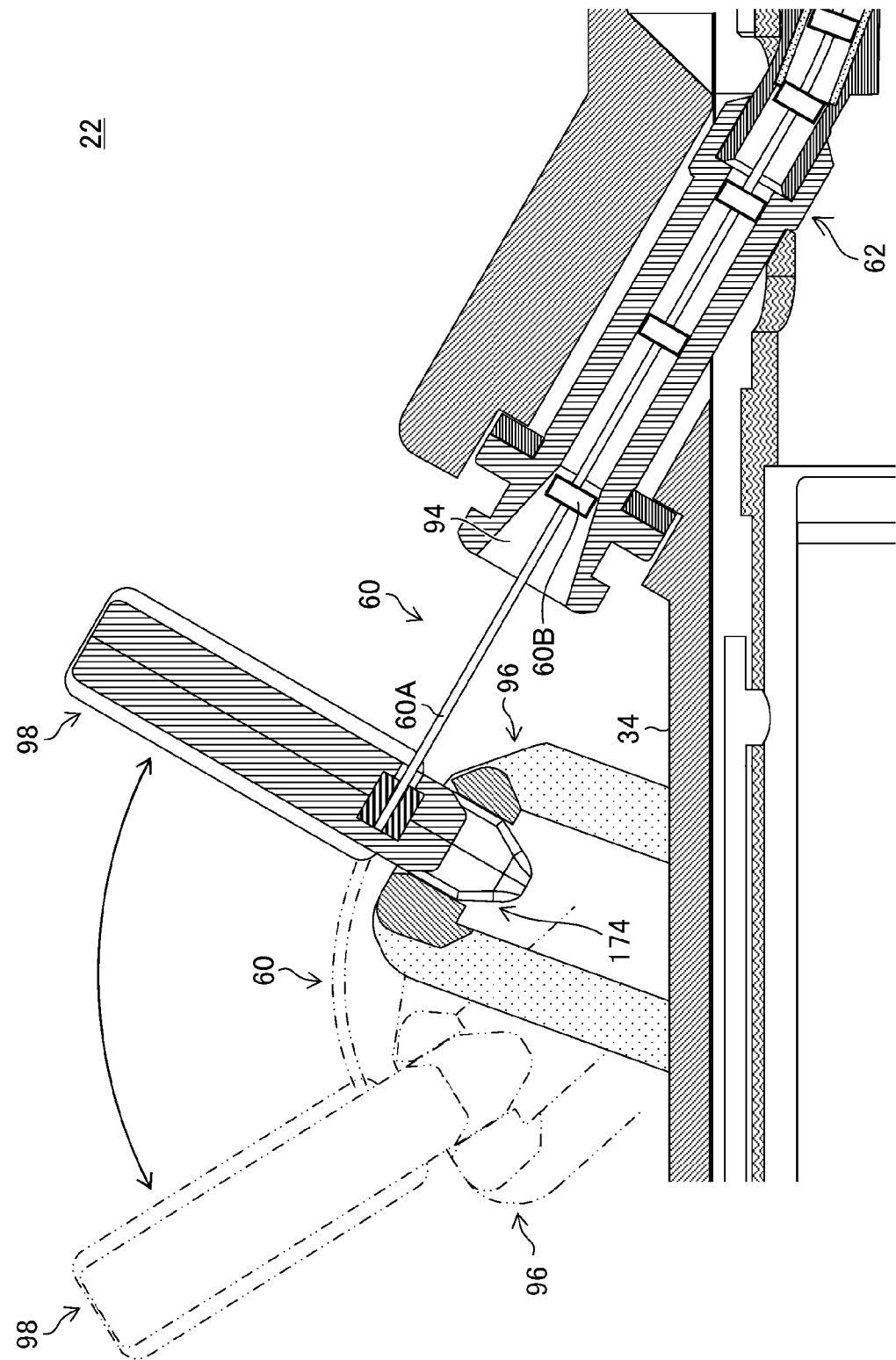
FIG. 24 is a main-part enlarged view around a lead-in port.
Figure 25:
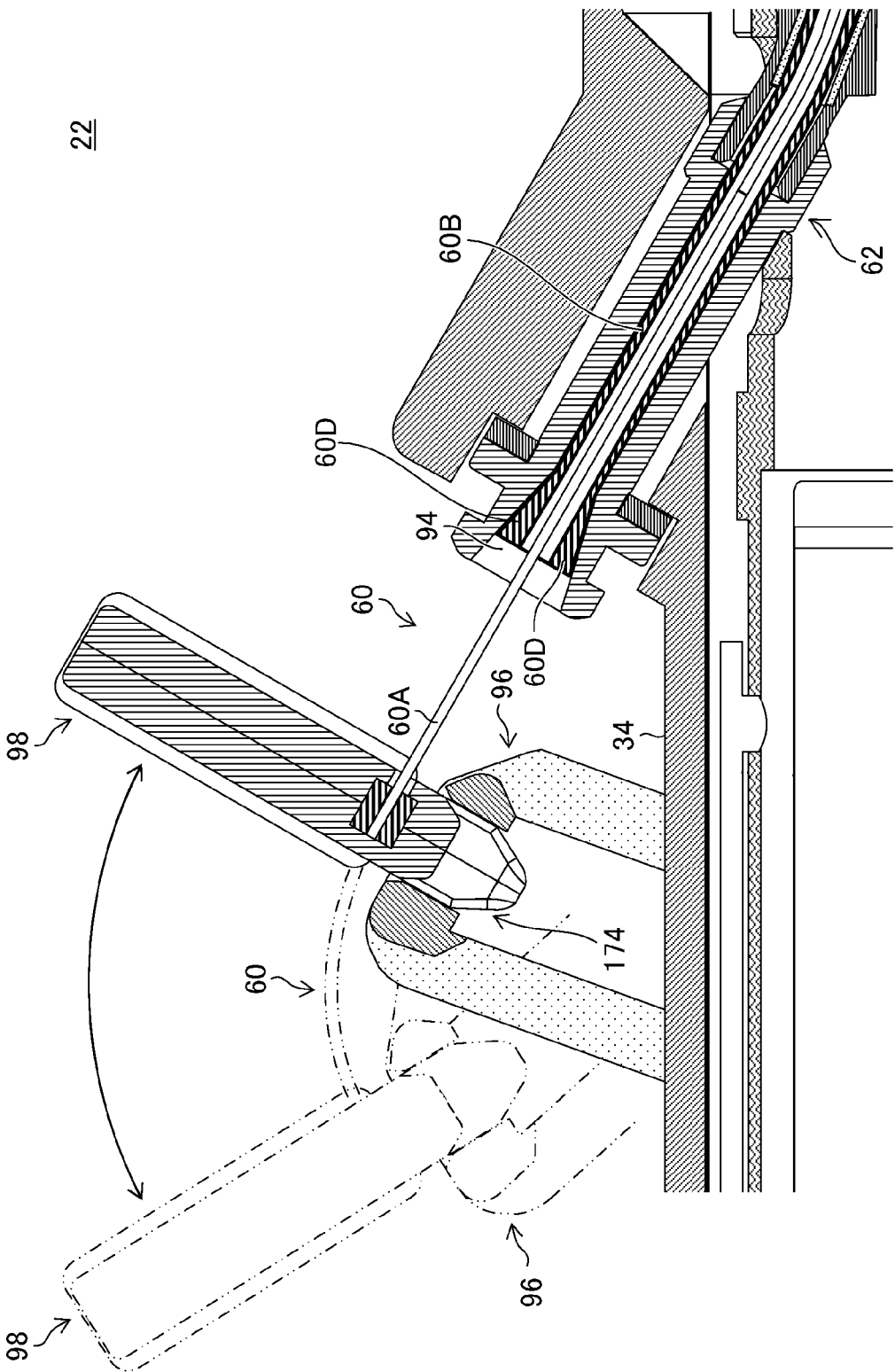
FIG. 25 is a main-part enlarged view around a lead-in port.

FIGS. 24 and 25 are main-part enlarged views around the lead-in port 94. In an aspect illustrated in FIG. 24, the wire 60 illustrated in FIG. 13 is inserted through the wire channel 62. In a state in which the movable member 96 is rotated to the distal end side, the erecting base 30 (not illustrated) is located at the lying position by the wire 60. When the erecting base 30 is lying, the gap filling member 60B located at the most proximal end is preferably located at the most distal end of the tapered lead-in port 94. Moreover, in addition to the above-described function of the meandering prevention member, the gap filling member 60B can also function as a backflow prevention member that prevents a fluid such as liquid in a body cavity which flows backward from the lead-out port 74 of the distal end member 28 via the wire channel 62 from leaking to the outside from the lead-in port 94.

In an aspect illustrated in FIG. 25, the wire 60 illustrated in FIG. 16 is inserted through the wire channel 62. As illustrated in FIG. 25, the second position regulation portion 60D provided at the gap filling member 60B comes into contact with the tapered lead-in port 94. The position of the gap filling member 60B is regulated. Moreover, in addition to the above-described meandering prevention function, the gap filling member 60B can also function as a backflow prevention member that prevents liquid in a body cavity which flows backward from the lead-out port 74 of the distal end member 28 via the wire channel 62 from leaking to the outside from the lead-in port 94.

Next, a coupling structure 210 according to a second embodiment is described with reference to FIGS. 26 to 29.

Figure 26:
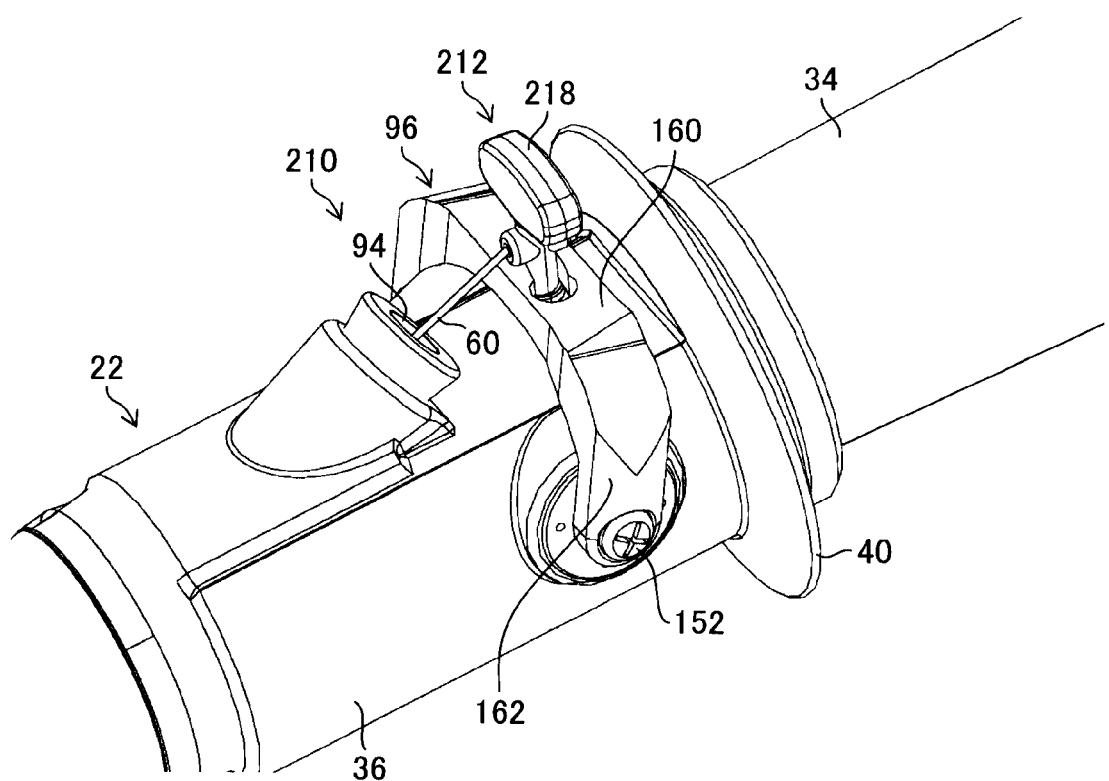
FIG. 26 is a perspective view of a coupling structure according to a second embodiment.
Figure 28:
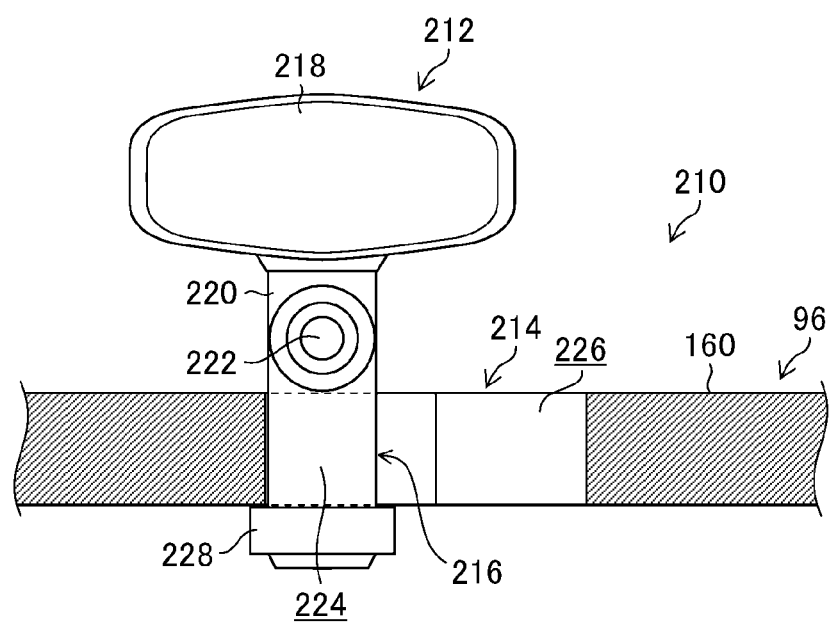
FIG. 28 is a main-part sectional view of the coupling structure illustrated in FIG. 26.

FIG. 26 is a perspective view of the coupling structure 210. FIG. 27 is an assembly perspective view of the coupling structure 210. FIG. 28 is a main-part sectional view of the coupling structure 210. The coupling structure 210 is described with the same reference signs applied to the same or similar members as or to those of the coupling structure 170 illustrated in FIGS. 11 to 21.

The coupling structure 210 is configured of a movable member 96 and an attachment member 212.

Referring to FIG. 27, an engagement hole 214 is provided in a beam portion 160 of the movable member 96, and an engagement portion 216 that is engaged with the engagement hole 214 in an attachable/detachable manner by a one-touch operation is provided at the attachment member 212. The attachment member 212 is configured of a pinch portion 218 and a shaft portion 220 configuring the engagement portion 216. The proximal end of the wire 60 is coupled to a hole portion 222 formed in the shaft portion 220.

Figure 29:
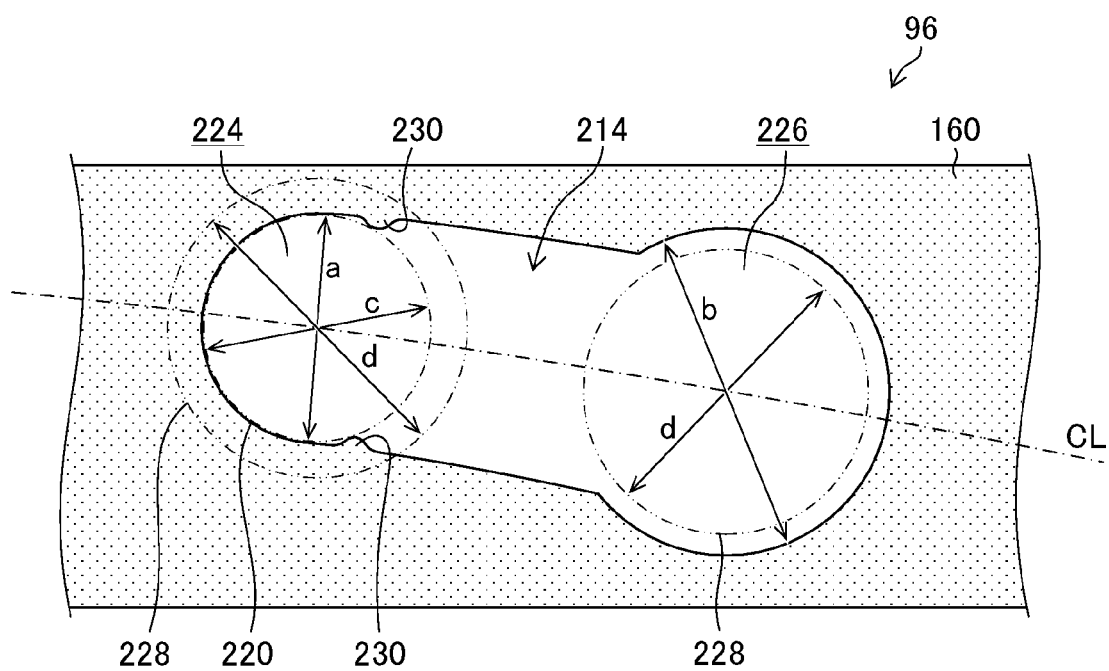
FIG. 29 is a plan view illustrating the size of an engagement portion with respect to an engagement hole.

The shape of the engagement hole 214 is described here. FIG. 29 is a plan view of the engagement hole 214, and illustrating a state in which the shape of the engagement portion 216 is superposed on the shape of the engagement hole 214.

The engagement hole 214 has a small width portion 224 having a diameter a and a large width portion 226 having a diameter b that is larger than the diameter a. In the embodiment, a first width according to the present invention is described as the diameter a, and a second width according to the present invention is described as the diameter b. As illustrated in FIG. 29, a line CL connecting the center of the small width portion 224 and the center of the large width portion 226 is a curved line. The line CL defines a substantial arc centered on the lead-in port 94 (not illustrated). The arrangement of the small width portion 224 and the large width portion 226 makes an operation easy when the attachment member 212 is engaged with the engagement hole 214. This will be described later.

The engagement portion 216 of the attachment member 212 illustrated in FIG. 27 has the shaft portion 220 having an outside diameter c that is equal to or smaller than the diameter a in FIG. 29, and a large diameter portion 228 provided at the distal end of the shaft portion 220. The large diameter portion 228 has an outside diameter d that is larger than the diameter a and smaller than the diameter b. The large diameter portion 228 functions as a fall prevention member that restricts detachment of the shaft portion 220 from the small width portion 224 in the axial direction of the shaft portion 220. To stably hold the shaft portion 220, the difference between the diameter a and the outside diameter c is preferably small.

The engagement operation is described. Since the large width portion 226 of the engagement hole 214 is larger than the large diameter portion 228, the engagement portion 216 of the attachment member 212 can be easily inserted into the engagement hole 214. Then, the attachment member 212 is slid from the large width portion 226 to the small width portion 224. At this time, as illustrated in FIG. 26, the attachment member 212 is fixed to the wire 60, and hence the attachment member 212 moves on a substantially arc-shaped locus centered on the lead-in port 94. Since the small width portion 224 and the large width portion 226 are arranged in a substantially arc form as described above, the attachment member 212 can smoothly slide between the small width portion 224 and the large width portion 226. Furthermore, when the attachment member 212 is located at the small width portion 224, a tension can be applied to the wire 60.

The engagement hole 214 has a frictional resistance portion 230 between the small width portion 224 and the large width portion 226. The frictional resistance portion 230 is provided at an opening entrance portion of the small width portion 224. The frictional resistance portion 230 can restrict unintentional sliding of the shaft portion 220 inserted into the small width portion 224, from the small width portion 224 to the large width portion 226. The frictional resistance portion 230 is formed to protrude from each of mutually facing wall surfaces of the engagement hole 214.

Even with the thus configured coupling structure 210, the attachment/detachment work of the attachment member 212 to/from the movable member 96 is performed outside the operation section 22 similarly to the coupling structure 170. The attachment work is of merely inserting the engagement portion 216 into the large width portion 226 of the engagement hole 214, sliding the engagement portion 216 toward the small width portion 224, and engaging the engagement portion 216 with the small width portion 224. Accordingly, the attachment member 212 can be engaged with the movable member 96 by a one-touch operation. With the attachment work, the proximal end of the wire 60 can be easily coupled to the movable member 96 via the attachment member 212.

When the engagement portion 216 is slid from the large width portion 226 toward the small width portion 224, the shaft portion 220 comes into contact with the frictional resistance portion 230. However, the engagement portion 216 can be properly engaged with the small width portion 224 by the force of sliding the engagement portion 216.

Moreover, in a state in which the engagement portion 216 is engaged with the small width portion 224, the large diameter portion 228 prevents the shaft portion 220 from being detached from the small width portion 224 in the axial direction of the shaft portion 220. Furthermore, since the shaft portion 220 comes into contact with the frictional resistance portion 230, sliding of the engagement portion 216 from the small width portion 224 to the large width portion 226 is restricted. Accordingly, the attachment member 212 can be reliably coupled to the movable member 96.

When the endoscope 10 is washed, to remove the attachment member 212 from the movable member 96, the engagement portion 216 of the attachment member 212 is slid from the small width portion 224 to the large width portion 226, and the engagement portion 216 is pulled out from the large width portion 226. Accordingly, the attachment member 212 is detached from the movable member 96 by a one-touch operation.

Thus, with the coupling structure 210 according to the second embodiment, compared with the endoscope of JP1994-315458A (JP-H6-315458A) and the endoscope of EP1759626B, the attachment/detachment operation of the proximal end of the wire 60 to/from the movable member 96 can be easily performed.

In FIG. 29, the engagement hole 214 including the frictional resistance portion 230 is illustrated as an example; however, the engagement hole 214 may not include the frictional resistance portion 230.

Next, a coupling structure 232 according to a third embodiment is described with reference to FIGS. 30 and 31.

FIG. 30 is an assembly perspective view of the coupling structure 232. FIG. 31 is a plan view of an engagement hole 214 formed in a movable member 96, and illustrating a state in which the shape of an engagement portion 236 of an attachment member 234 is superposed on the shape of the engagement hole 214. The coupling structure 232 is described with the same reference signs applied to the same or similar members as or to those of the coupling structure 210 illustrated in FIGS. 26 to 29.

Figure 31:
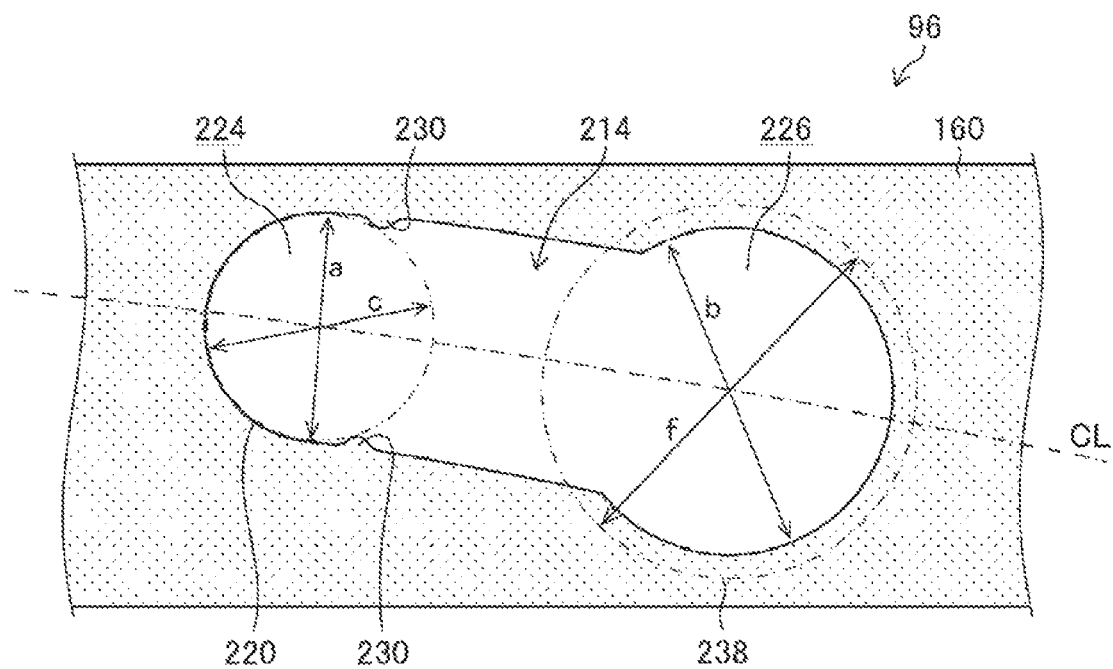
FIG. 31 is a plan view of an engagement hole illustrating the size of an engagement portion with respect to the engagement hole.

As illustrated in FIG. 31, the engagement hole 214 has a small width portion 224 having a diameter a and a large width portion 226 having a diameter b that is larger than the diameter a. The small width portion 224 and the large width portion 226 have a positional relationship similar to that illustrated in FIG. 25.

The engagement portion 236 of the attachment member 234 illustrated in FIG. 30 has a shaft portion 220 having an outside diameter c that is equal to or smaller than the diameter a, and a large diameter portion 238 provided at the distal end of the shaft portion 220 and having an outside diameter f that is larger than the diameter b. A plurality of (for example, four) slotting grooves 237 (see FIG. 30) are formed in the large diameter portion 238. When the large diameter portion 238 is fitted into the large width portion 226, the large diameter portion 238 is elastically deformed by the plurality of slotting grooves 237 and the diameter of the large diameter portion 238 is decreased. To stably hold the shaft portion 220, the difference between the diameter a and the outside diameter c is preferably small.

Even with the thus configured coupling structure 232, the attachment/detachment work of the attachment member 234 to/from the movable member 96 is performed outside the operation section 22 similarly to the coupling structure 210. The attachment work is of first fitting the large diameter portion 238 into the large width portion 226 of the engagement hole 214. At this time, the large diameter portion 238 is elastically deformed by the plurality of slotting grooves 237 and the diameter of the large diameter portion 238 is decreased. Accordingly, after the large diameter portion 238 is passing through the large width portion 226 and then the large diameter portion 238 has passed through the large width portion 226, the diameter of the large diameter portion 238 is restored to the original diameter. Thus, the large diameter portion 238 is engaged with a back surface 160A of a beam portion 160 of the movable member 96. The attachment member 234 is prevented from coming out from the movable member 96.

Then, the engagement portion 236 is slid toward the small width portion 224, and the engagement portion 236 is engaged with the small width portion 224. Accordingly, the attachment member 234 can be engaged with the movable member 96 by a one-touch operation. With the attachment work, the proximal end of the wire 60 can be easily coupled to the movable member 96 via the attachment member 234.

Moreover, in a state in which the engagement portion 236 is engaged with the small width portion 224, the large diameter portion 238 prevents the shaft portion 220 from being detached from the small width portion 224 in the axial direction of the shaft portion 220. Furthermore, since the shaft portion 220 comes into contact with the frictional resistance portion 230, sliding of the engagement portion 236 from the small width portion 224 to the large width portion 226 is restricted. Accordingly, the attachment member 234 can be reliably coupled to the movable member 96.

When the endoscope 10 is washed, to remove the attachment member 234 from the movable member 96, the engagement portion 236 of the attachment member 234 is slid from the small width portion 224 to the large width portion 226, then the large diameter portion 238 is pinched with fingers to decrease the diameter of the large diameter portion 238, and the large diameter portion 238 is pulled out from the large width portion 226. Accordingly, the attachment member 234 is detached from the movable member 96 by a one-touch operation.

Thus, with the coupling structure 232 according to the third embodiment, compared with the endoscope of JP1994-315458A (JP-H6-315458A) and the endoscope of EP1759626B, the attachment/detachment operation of the proximal end of the wire 60 to/from the movable member 96 can be easily performed.

In FIG. 31, the engagement hole 214 including the frictional resistance portion 230 is illustrated as an example; however, the engagement hole 214 may not include the frictional resistance portion 230.

Next, a coupling structure 240 according to a fourth embodiment is described with reference to FIGS. 32 and 33.

Figure 32:
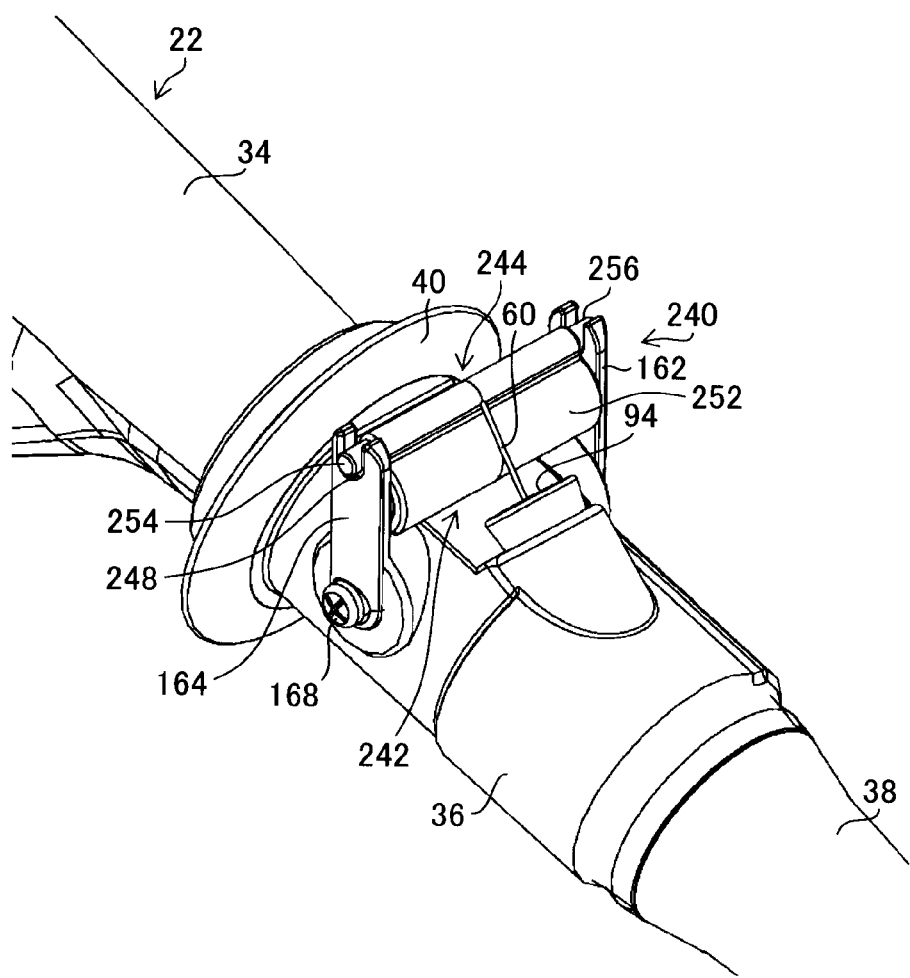
FIG. 32 is a perspective view of a coupling structure according to a fourth embodiment.
Figure 33:
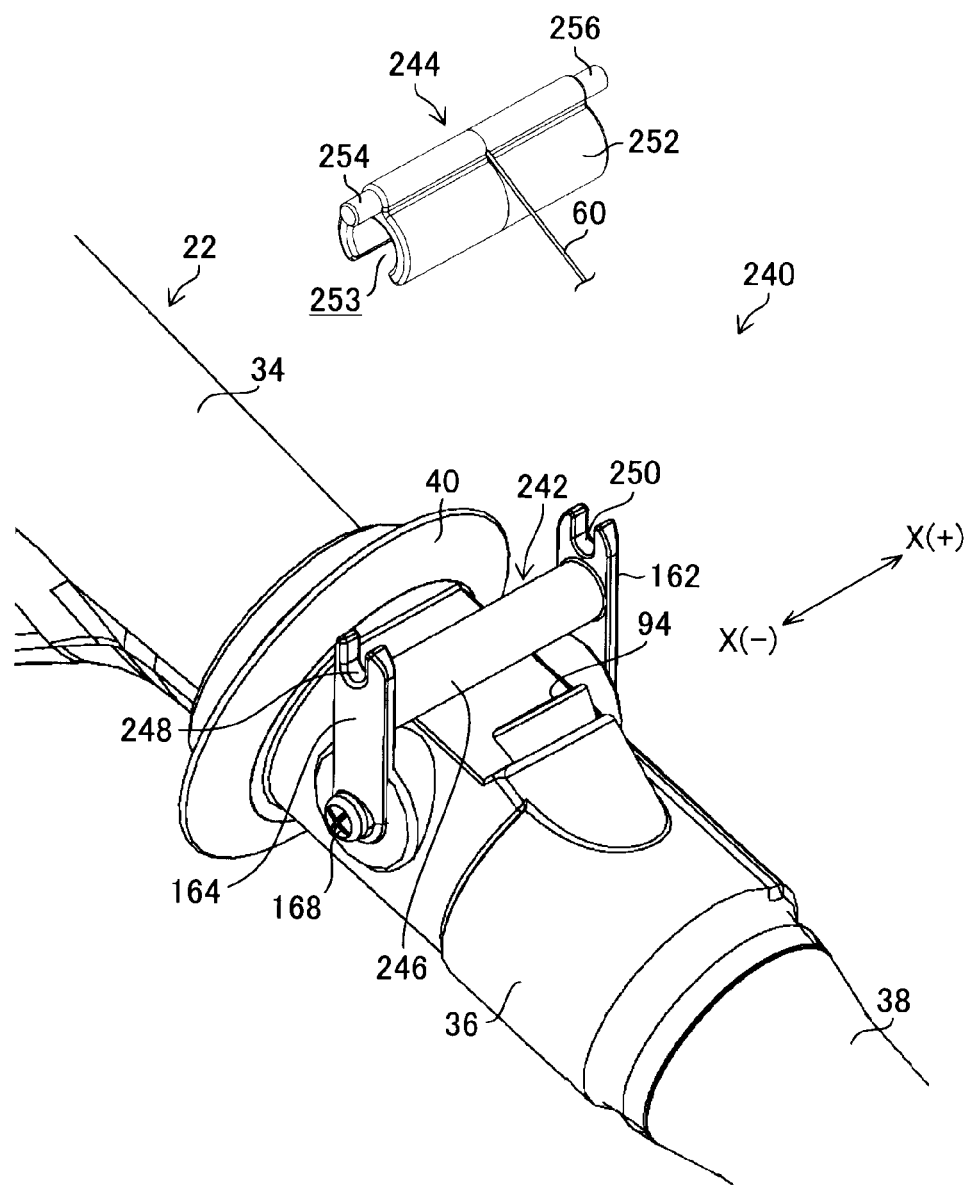
FIG. 33 is an assembly perspective view of the coupling structure illustrated in FIG. 32.

FIG. 32 is a perspective view of the coupling structure 240. FIG. 33 is an assembly perspective view of the coupling structure 240. The coupling structure 240 is described with the same reference signs applied to the same or similar members as or to those of the coupling structure 170 illustrated in FIGS. 11 to 21.

The coupling structure 240 is configured of a movable member 242 serving as a movable member, and an attachment member 244.

The movable member 242 is configured of a leg portion 162, a leg portion 164, and a cylindrical body 246 that couples the leg portion 162 and the leg portion 164 to each other. The cylindrical body 246 extends in a direction (X(+)-X(−) direction) perpendicular to the axial direction of the wire 60. Moreover, as illustrated in FIGS. 32 and 33, U-shaped grooves 248 and 250 configuring a rotation restriction stopper are formed in upper end portions of the leg portion 162 and the leg portion 164.

The proximal end of the wire 60 is coupled to the attachment member 244. The attachment member 244 is configured of a ring-shaped body 252 that is rotatably engaged with the outer periphery of the cylindrical body 246, and pins 254 and 256 that configure the rotation restriction stopper together with the grooves 248 and 250. The ring-shaped body 252 has a C-like shape in a section orthogonal to the longitudinal direction. By pressing a slit 253 that is formed in the ring-shaped body 252 in the longitudinal direction against the cylindrical body 246, the diameter of the ring-shaped body 252 is increased and is engaged with the cylindrical body 246 by a one-touch operation.

Even with the thus configured coupling structure 240, the attachment/detachment work of the attachment member 244 to/from the movable member 242 is performed outside the operation section 22 similarly to the coupling structures 170 and 210. The attachment work is of pressing the slit 253 of the ring-shaped body 252 of the attachment member 244 against the cylindrical body 246 of the movable member 242. With the work, the attachment member 244 is engaged with the movable member 242 by a one-touch operation. Accordingly, the proximal end of the wire 60 can be reliably coupled to the movable member 242 via the attachment member 244.

Moreover, when the ring-shaped body 252 is engaged with the cylindrical body 246, the pin 254 is engaged with the groove 248 and the pin 256 is engaged with the groove 250 simultaneously. When the wire 60 is operated to be pushed or pulled by the movable member 242, the ring-shaped body 252 can be prevented from being rotated relative to the cylindrical body 246. Accordingly, the pushing/pulling operation of the wire 60 can be smoothly performed.

When the endoscope 10 is washed, to remove the attachment member 244 from the movable member 242, the attachment member 244 is pulled in a direction in which the pins 254 and 256 are removed from the grooves 248 and 250, hence the ring-shaped body 252 is pushed by the cylindrical body 246, the diameter of the ring-shaped body 252 is increased, and the ring-shaped body 252 is removed from the cylindrical body 246. Accordingly, the attachment member 244 is detached from the movable member 242 by a one-touch operation.

Thus, with the coupling structure 240 according to the third embodiment, compared with the endoscope of JP1994-315458A (JP-H6-315458A) and the endoscope of EP1759626B, the attachment/detachment operation of the proximal end of the wire 60 to/from the movable member 242 can be easily performed.

In the above-described embodiment, the cylindrical body 246 is provided at the movable member 242, and the ring-shaped body 252 is provided at the attachment member 244. However, the cylindrical body 246 may be provided at one of the movable member 242 and the attachment member 244, and the ring-shaped body 252 may be provided at the other one.

In the above-described embodiments, the wire 126 is an example of a drive member of the erecting operation mechanism 120 as illustrated in FIGS. 9 and 10. However, a link mechanism may be employed instead of the wire 126.

Figure 34:
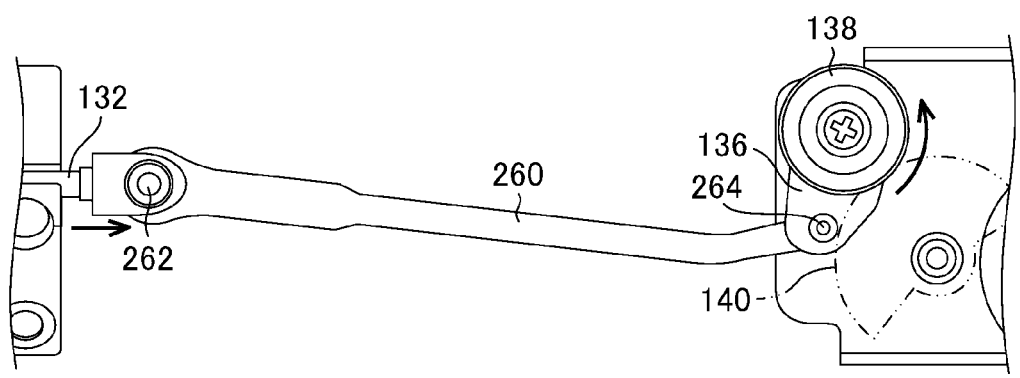
FIG. 34 illustrates a main-part structure in which a first slider and a lever are coupled to each other by using a link sheet metal serving as a link mechanism.

FIG. 30 illustrates a main-part structure in which a first slider 132 and a lever 136 are coupled to each other by using a link sheet metal 260 serving as a link mechanism. FIG. 34 is a movement explanatory diagram of the link mechanism in FIG. 35.

Figure 35:
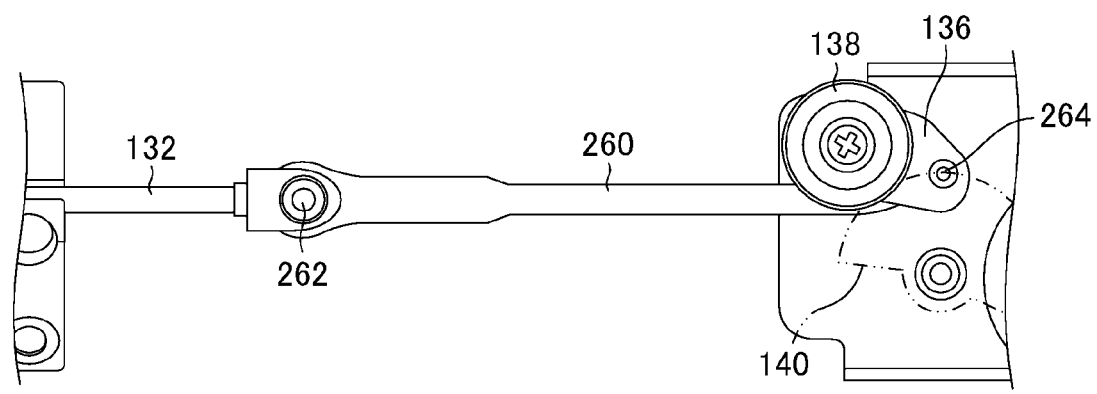
FIG. 35 is a movement explanatory diagram of the link mechanism in FIG. 34.

As illustrated in FIGS. 34 and 35, the distal end of the link sheet metal 260 is rotatably coupled to the proximal end of the first slider 132 via a pin 262, and the proximal end of the link sheet metal 260 is rotatably coupled to the lever 136 via a pin 264.

Accordingly, when the erecting operation lever 20 illustrated in FIGS. 9 and 10 is rotated, a straight advancement motion of the first slider 132 can be transmitted to the lever 136 via the link sheet metal 260 serving as the link mechanism. Thus, the lever 136 is rotated in a rotation range from FIG. 34 to FIG. 35. The resultant rotational force can be transmitted to, for example, the movable member 96 illustrated in FIGS. 9 and 10.

In the above-described embodiments, a duodenum endoscope is described as an example of the endoscope 10. However, the present invention can be applied to any one of various endoscopes, such as an ultrasonic endoscope, as long as the endoscope includes an erecting base that adjusts a lead-out direction of a treatment tool, at a distal end part of an insertion section.

REFERENCE SIGNS LIST 10 endoscope
12 endoscope system
14 processor device
16 light source device
18 display
20 erecting operation lever
22 operation section
22A one side surface
22B the other side surface
24 insertion section
26 distal end part
28 distal end member
28A peripheral surface
30 erecting base
30A guide surface
30B base portion
32 operation section main body
34 holding part
36 extension part
38 break prevention pipe
38A proximal end portion
40 flange
42 treatment tool lead-in port
44 mount portion
44A distal end portion
46 universal cord
48 electric connector
50 light source connector
52 bending part
54 soft part
56 treatment tool
56A distal end portion
58 treatment tool channel
60 wire
60A wire body
60B gap filling member
60C first position regulation portion
60D second position regulation portion
62 wire channel
64 angle knob
66 air/water supply button
68 suction button
70 air/water supply nozzle
72 treatment tool lead-out port
74 lead-out port
76 cap 76A opening window
78 partition wall
78A bearing portion
80 partition wall
80A bearing portion
82 erecting base housing chamber
84 rotation shaft
86 rotation shaft
88 optical system housing chamber
90 illumination window
92 observation window
94 lead-in port
96 movable member
98 attachment member
98A attachment member
100 engagement member
102 housing groove
104 opening
106 engagement guide portion
108 engagement guide path
110 deformation generation portion
112 groove
114 groove
116 detachment guide surface
120 erecting operation mechanism
124 first conversion mechanism
126 wire
128 second conversion mechanism
130 crank member
132 first slider
134 second slider
136 lever
138 first gear
140 second gear
142 third gear
144 fourth gear
146 bracket
148 shaft
150 shaft
152 drive shaft
160 beam portion
160A back surface
162 leg portion
164 leg portion
166 O-ring
168 driven shaft
170 coupling structure
170A coupling structure
172 wire assembly
174 engagement hole
174A engagement hole
175 edge portion
176 engagement portion
176A engagement portion
177 tubular portion
178 core portion
180 hole portion
182 cut portion
184 elastic deformation portion
184A slotted portion
186 claw portion
186A claw portion
187 tapered portion
200 branch pipe
202 distal end pipe
204 pipe line
206 pipe line
208 suction pipe
210 coupling structure
212 attachment member
214 engagement hole
216 engagement portion
218 pinch portion
220 shaft portion
222 hole portion
224 small width portion
226 large width portion
228 large diameter portion
230 frictional resistance portion
232 coupling structure
234 attachment member
236 engagement portion
237 slotting groove
238 large diameter portion
240 coupling structure
242 movable member
244 attachment member
246 cylindrical body
248 groove
250 groove
252 ring-shaped body
253 slit
254 pin
256 pin
260 link sheet metal
262 pin
264 pin
P pitch

What is claimed is:

1. An endoscope comprising:
an operation section provided with an operating member;
an insertion section that is provided on a distal end side of the operation section and that is inserted into a subject;
a treatment tool erecting base provided at a distal end part of the insertion section;
a driven lever, comprising a beam, that is arranged to be exposed to outside of the operation section and that moves in association with an operation of the operating member;
a proximal end opening provided in the operation section;
a distal end opening provided in the distal end part;
an erecting operation wire channel that is provided in the insertion section and that causes the proximal end opening to communicate with the distal end opening;
an erecting operation wire that is inserted through the erecting operation wire channel, wherein a distal end side of the erecting operation wire is arranged outside the distal end opening, and the distal end side of the erecting operation wire is coupled to the treatment tool erecting base, a proximal end side of the erecting operation wire is arranged outside the proximal end opening and the proximal end side of the erecting operation wire is coupled to the driven lever, and the erecting operation wire is pushed or pulled in accordance with a movement of the driven lever to move the treatment tool erecting base; and
an attachment member, comprising a plate-shaped body, that is provided at a proximal end of the erecting operation wire and that is engaged with the driven lever in an attachable/detachable manner by a one-touch operation, wherein the erecting operation wire has
a flexible long wire body, and
a plurality of gap filling members that is arranged at least a portion in an axial direction of the flexible long wire body and that is formed to have a diameter larger than an outside diameter of the flexible long wire body and smaller than an inside diameter of the erecting operation wire channel, wherein the plurality of gap filling members are peripherally surrounding the wire body,
wherein the plurality of gap filling members function as backflow prevention members that prevent a fluid from flowing backward from the distal end opening to the proximal end opening in the erecting operation wire channel.

2. The endoscope according to claim 1 wherein the plurality of gap filling members functions as a meandering prevention member that prevents the flexible long wire body from meandering by coming into contact with an inner surface of the erecting operation wire channel.

3. The endoscope according to claim 1 wherein the plurality of gap filling members are provided at mutually different positions in the axial direction of the flexible long wire body.

4. The endoscope according to claim 1, wherein the plurality of gap filling members is a columnar or spherical expansion portion provided at the flexible long wire body.

5. The endoscope according to claim 1, wherein the plurality of gap filling members is a long outer layer member that is disposed on an outer periphery side of the flexible long wire body and that extends in the axial direction of the flexible long wire body.

6. The endoscope according to claim 5, wherein the long outer layer member is a tubular body through which the flexible long wire body is inserted to allow the flexible long wire body to freely advance/retract therethrough.

7. The endoscope according to claim 6, wherein the flexible long wire body has a first position regulation portion that regulates a position of the tubular body in the axial direction of the flexible long wire body.

8. The endoscope according to claim 6,
wherein the tubular body has a second position regulation portion that regulates a position of the tubular body in a longitudinal direction of the erecting operation wire channel.

9. The endoscope according to claim 1,
wherein an engagement hole is provided in one of the driven lever and the attachment member, and an engagement portion comprising a surface that is engaged with a surface of the engagement hole in the attachable/detachable manner is provided at the other one.

10. The endoscope according to claim 9,
wherein the engagement portion is provided with an elastic deformation portion that is elastically deformed and engaged with the engagement hole.

11. The endoscope according to claim 10,
wherein a pair of claw portions are formed at the elastic deformation portion, the pair of claw portions being elastically deformable and configured to be latched to an edge portion of the engagement hole, the pair of claw portions being displaced in directions to move toward each other by elastic deformation when the engagement portion is engaged with or disengaged from the engagement hole.

12. The endoscope according to claim 9, wherein:
the engagement hole has a small width portion having a first width, and a large width portion having a second width that is larger than the first width; and
the engagement portion has a shaft portion having an outside diameter that is smaller than the first width, and a large diameter portion provided at a distal end of the shaft portion and having an outside diameter that is larger than the first width and smaller than the second width.

13. The endoscope according to claim 1, wherein:
one of the driven lever and the attachment member is provided with a cylindrical body extending in a direction perpendicular to an axial direction of the erecting operation wire, and the other one is provided with a ring-shaped body that is rotatably engaged with an outer periphery of the cylindrical body; and
the endoscope comprises a rotation restriction stopper that restricts relative rotations of the cylindrical body and the ring-shaped body.

14. The endoscope according to claim 1, further comprising:
an engagement member provided at a distal end of the erecting operation wire; and
a housing groove that is provided in the treatment tool erecting base and that is engaged with the engagement member in an engageable/disengageable manner.

15. The endoscope according to claim 1,
wherein the driven lever is rotatably provided while a direction perpendicular to an axial direction of the erecting operation wire serves as a rotation axis.

16. The endoscope according to claim 15, wherein:
the operating member is rotatably supported by the operation section; and
the endoscope further comprises:
a first conversion mechanism that converts a rotational motion of the operating member into a linear motion,
a wire that is linearly driven by the first conversion mechanism, and
a second conversion mechanism that converts a linear motion of the wire into a rotational motion to rotate the driven lever.

17. The endoscope according to claim 16,
wherein the second conversion mechanism includes a speed reduction mechanism, comprising a gear.

* * * * *